United States Patent
Tanaka et al.

(10) Patent No.: US 10,280,188 B2
(45) Date of Patent: May 7, 2019

(54) FLUORINE-CONTAINING BISPHOSPHONIC ACID DERIVATIVE AND USE THEREOF

(71) Applicant: NAGASAKI UNIVERSITY, Nagasaki-shi, Nagasaki (JP)

(72) Inventors: Yoshimasa Tanaka, Nagasaki (JP); Satoshi Mizuta, Nagasaki (JP); Hiroshi Ueda, Nagasaki (JP)

(73) Assignee: Nagasaki University, Nagasaki (JP)

( * ) Notice: Subject to any disclaimer, the term of this patent is extended or adjusted under 35 U.S.C. 154(b) by 0 days.

(21) Appl. No.: 15/548,303

(22) PCT Filed: Feb. 1, 2016

(86) PCT No.: PCT/JP2016/052960
§ 371 (c)(1),
(2) Date: Aug. 2, 2017

(87) PCT Pub. No.: WO2016/125757
PCT Pub. Date: Aug. 11, 2016

(65) Prior Publication Data
US 2018/0022769 A1  Jan. 25, 2018

(30) Foreign Application Priority Data
Feb. 2, 2015  (JP) .................... 2015-018260

(51) Int. Cl.
*A61K 35/17* (2015.01)
*A61K 31/683* (2006.01)
*C07F 9/6506* (2006.01)
*C07F 9/38* (2006.01)

(52) U.S. Cl.
CPC .......... *C07F 9/6506* (2013.01); *A61K 31/683* (2013.01); *A61K 35/17* (2013.01); *C07F 9/3873* (2013.01)

(58) Field of Classification Search
CPC .................................................. C07F 9/6506
See application file for complete search history.

(56) References Cited

U.S. PATENT DOCUMENTS

| 8,816,082 B2 | 8/2014 | Tsantrizos et al. |
| 2007/0275931 A1 | 11/2007 | Oldfield et al. |
| 2011/0230443 A1 | 9/2011 | Ebetino et al. |

FOREIGN PATENT DOCUMENTS

| JP | 2010-523709 A | 7/2010 |
| JP | 2012-503022 A | 2/2012 |
| WO | WO 2011/147038 A1 | 12/2011 |

OTHER PUBLICATIONS

Inoue et al. "New Synthesis of gem-Bis(phosphono)ethylenes and their Applications" Synthesis, 2003, No. 13, pp. 1971-1976.*

Atack et al. "Effects of L-690,448, a Prodrug of the Bisphosphonate Inositol Monophosphatase Inhibitor L-690,330, on Phosphatidylinositol Cycle Markers" The Journal of Pharmacology and Experimental Therapeutics, 1994, vol. 270, No. 1, pp. 70-76.*
Bala et al., "Synthesis of a Novel Bisphosphonic Acid Alkene Monomer," *Synthetic Communications*, 40(23): 3577-3584 (2010).
Beier et al., "A new route to α-alkyl-α-fluoromethylenebisphosphonates," *Org. Biomol. Chem.*, 9(11): 4035-4038 (2011).
De Schutter et al., "Novel bisphosphonate inhibitors of the human farnesyl pyrophosphate synthase," *Bioorg Med. Chem. Lett.*, 20(19): 5781-5786 (2010).
Gnant et al., "Endocrine Therapy plus Zoledronic Acid in Premenopausal Breast Cancer," *N. Engl. J. Med.*, 360(7): 679-691 (2009).
Kunzmann et al., "γ/σ T-Cell Stimulation by Pamidronate," *N. Engl. J. Med.*, 340(9): 737-738 (1999).
Lin et al., "Design and Synthesis of Active Site Inhibitors of the Human Farnesyl Pyrophosphate Synthase: Apoptosis and Inhibition of ERK Phosphorylation in Multiple Myeloma Cells," *J. Med. Chem.*, 55(7): 3201-3215 (2012).

(Continued)

*Primary Examiner* — Joseph R Kosack
(74) *Attorney, Agent, or Firm* — Leydig, Voit & Mayer, Ltd.

(57) ABSTRACT

A series of fluorine-containing bisphosphonic acids in which an alkylamine side chain is added, a series of fluorine-containing bisphosphonic acids in which an amino group substituted by a heterocyclic group or a heterocyclic group containing a nitrogen atom is added, to the carbon atom of P—C(F)—P, and a series of fluorine-containing bisphosphonate derivatives in which the acid moiety thereof is esterified by an alkoxymethyl group such as POM group, n-butanoyloxymethyl (BuOM) group and the like, that is, the fluorine-containing bisphosphonic acid and fluorine-containing bisphosphonate derivative represented by the following formula (I):

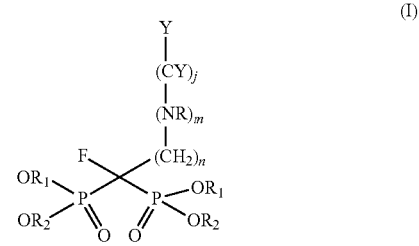

wherein each symbol is as defined in the DESCRIPTION, can efficiently induce proliferation of peripheral blood γδ T cells that express Vγ2Vδ2 T cell receptor having superior cytotoxicity against tumor cells and virus infected cells, immunize tumor cells and virus infected cells, and can induce cytotoxicity by γδ T cells.

11 Claims, 13 Drawing Sheets

(56) References Cited

OTHER PUBLICATIONS

Marma et al., "Synthesis and Biological Evaluation of α-Halogenated Bisphosphonate and Phosphonocarboxylate Analogues of Risedronate," *J. Med. Chem.*, 50(24): 5967-5975 (2007).

Morgan et al., "First-line treatment with zoledronic acid as compared with clodronic acid in multiple myeloma (MRC Myeloma IX): a randomised controlled trial," *Lancet*, 376(9757): 1989-1999 (2010).

Szajnman et al., "1-(Fluoroalkylidene)-1,1-bisphosphonic acids are potent and selective inhibitors of the enzymatic activity of *Toxoplasma gondii* farnesyl pyrophosphate synthase," *Org. Biomol. Chem.*, 10(7): 1424-1433 (2012).

Wang et al., "Butyrophilin 3A1 Plays an Essential Role in Prenyl Pyrophosphate Stimulation of Human Vγ2Vσ2 T Cells," *J. Immunol.*, 191(3): 1029-1042 (2013).

Japanese Patent Office, International Search Report in International Patent Application No. PCT/JP2016/052960 (dated Apr. 26, 2016).

\* cited by examiner (1)

(2)

(3)

(4)

(5)

anti-Vδ2 antibody (green fluorescence)

anti-Vδ2 antibody (green fluorescence)

E/T ratio

FLUORINE-CONTAINING BISPHOSPHONIC ACID DERIVATIVE AND USE THEREOF

CROSS-REFERENCE TO RELATED APPLICATIONS

This patent application is the U.S. national phase of International Patent Application No. PCT/JP2016/052960, filed on Feb. 1, 2016, which claims the benefit of Japanese Patent Application No. 2015-018260, filed Feb. 2, 2015, the disclosures of which are incorporated herein by reference in their entireties for all purposes.

TECHNICAL FIELD

The present invention relates to novel fluorine-containing bisphosphonate derivatives and use thereof. More particularly, the present invention relates to fluorine-containing bisphosphonic acids, fluorine-containing bisphosphonate ester derivatives and pharmaceutical compositions, lymphocyte-treating agents, antitumor immune cell therapy agents, anti viral infection immune cell therapy agents and the like, each containing said derivative as an active ingredient.

BACKGROUND ART

Bisphosphonic acids are a group of compounds having a P—C—P skeleton, and show high bone tissue penetration and high affinity for bone. In addition, when the first generation bisphosphonic acids such as etidronic acid, clodronic acid and the like are selectively incorporated into monocytic cells such as osteoclasts and the like by liquid-phase endocytosis, they are metabolically converted to ATP analogs, act antagonistically to ATP receptors and show cytotoxicity. Thus, the first generation bisphosphonic acids suppress bone resorption by inducing cell death in osteoclasts. Utilizing such property, bisphosphonic acids are applied to various bone-related diseases. To be specific, they are used as prophylactic or therapeutic drugs for diseases relating to the fragility of bone and calcium concentration variation such as osteoporosis, osteitis deformans, osteogenesis imperfecta and hypercalcemia in malignant tumor. In addition, bisphosphonic acids belonging to the second generation such as pamidronic acid, alendronic acid, ibandronic acid and the like, and bisphosphonic acids belonging to the third generation such as risedronic acid, zoledronic acid and the like contain a nitrogen atom in the side chain, and are called nitrogen-containing bisphosphonic acids. When these bisphosphonic acids are selectively incorporated into monocytic cells such as osteoclast and the like, they specifically inhibit farnesyl diphosphate synthase and show cytotoxicity. Utilizing the properties thereof, various nitrogen-containing bisphosphonic acids have been used as improving-drugs for osteoporosis and hypercalcemia in malignant tumor. Recently, moreover, it has been reported that the disease-free survival is preferentially extended when zoledronic acid is used as an adjuvant therapy drug in the endocrine therapy and chemotherapy of premenopausal estrogen sensitive early breast cancer cases and multiple myeloma (non-patent documents 1, 2). This is considered to be because nitrogen-containing bisphosphonic acid has direct cytotoxicity and/or indirect cytotoxicity via activation of immunocytes on tumor cells and shows an antitumor effect.

For example, a part of etidronic acid or clodronic acid administered to a living body enters into the cell by a fluid phase endocytosis action, is transferred to nucleoside monophosphate, and converted to a nucleoside triphosphate analog compound. A metabolite thereof is shown to antagonistically inhibit biological enzyme reaction utilizing high energy phosphate bond of nucleoside triphosphate. When the incorporating cell is osteoclast, bone resorption is suppressed, and the concentration of calcium in the plasma decreases. In the case of tumor cells, the tumor cells are injured and a direct antitumor effect is expected.

The second generation and third generation nitrogen-containing bisphosphonic acids transferred into the cell have been shown to inhibit farnesyl diphosphate synthase involved in the biosynthesis pathway of isoprenoidal metabolites such as cholesterol and the like. Such enzyme catalyzes a reaction to synthesize geranyl diphosphate from isopentenyl diphosphate and dimethylallyl diphosphate, and a reaction to synthesize farnesyl diphosphate from isopentenyl diphosphate and geranyl diphosphate. Therefore, inhibition of farnesyl diphosphate synthase is considered to shut off the metabolic pathway located downstream of geranyl diphosphate, as well as cause accumulation of isopentenyl diphosphate to be an enzyme substrate. When the biosynthesis pathway located downstream of geranyl diphosphate is shut off, isoprenoidal compounds such as cholesterol, liposoluble vitamins, bile acid, lipoprotein and the like are not biosynthesized, and the proliferation of tumor cells is considered to be suppressed.

Generally, the isopropenyl group of farnesyl diphosphate and geranylgeranyl diphosphate biosynthesized by farnesyl diphosphate synthase is transferred to, what is called, small G proteins such as Ras, Rho, Rap, Rab, Rac and the like. The small G protein having the transferred isopropenyl group is translocated to a cellular membrane, which is an inherent action site of small G protein, since the isopropenyl group functions as a cellular membrane anchor, and exhibits important physiological functions such as cell proliferation, adhesion and the like. However, when nitrogen-containing bisphosphonic acid such as zoledronic acid and the like inhibits farnesyl diphosphate synthase, transfer of the isopropenyl group is inhibited, translocation to the membrane of small G protein is prevented, and, as a result, tumor cell proliferation is inhibited. This is one of the mechanisms that explain direct antitumor effects shown by nitrogen-containing bisphosphonic acid.

When farnesyl diphosphate synthase is further inhibited, the intracellular concentration of isopentenyl diphosphate as a substrate thereof increases. The increase in the intracellular concentration of isopentenyl diphosphate is detected by a butyrophilin 3A1 transmembrane type protein, and the change thereof is recognized by γδ T cells having a Vγ2Vδ2 T cell receptor (non-patent documents 3, 4). As a result, the γδ T cells are degranulated to release perforin and granzyme B, which induces apoptosis of tumor cells and virus infected cells. It is shown that nitrogen-containing bisphosphonic acid indirectly and efficiently damage tumor cells and virus-infected cells via activation of immunocyte.

The direct and indirect cytotoxicity by the nitrogen-containing bisphosphonic acids as mentioned above depends on the degree of incorporation into the cells to be injured, and the degree of inhibition of farnesyl diphosphate synthase. However, since bisphosphonic acids clinically applicable at present have all been synthesized for the purpose of improving bone-related disease, synthesis and screening of the compounds was performed using the affinity to bone, which is the action site of osteoclast, and cytotoxicity to osteoclast as indices. However, in the development of medicaments against tumor and virus infection, high bone penetration is conversely a factor that decreases reachability to tumor cells and virus infected cells.

Therefore, when direct improvement of cytotoxicity is desired, a decrease in the bone penetration needs to be one goal. On the other hand, when improvement of activation of γδ T cell as an immunity effector is desired, it is necessary to develop drugs by using, as indices, uptake into monocyte cells to be antigen presenting cells and γδ T cells activation potency. Thus, for compound screening without using suppression of bone resorption as an index, systematic synthesis of bisphosphonic acid having a basic skeleton different from that of conventional bisphosphonic acid is necessary.

About 30% of the low molecular medicaments currently on the market have fluorine in the basic skeleton. The reason for the superiority of medicaments due to the presence of a fluorine atom has not been completely elucidated. Until now, however, in the developmental stage of bisphosphonic acid, the fluorine-containing bisphosphonic acid is only one in which the hydroxyl group bonded to C in the P—C—P skeleton of risedronic acid is substituted by fluorine. This is because introduction of a fluorine atom is synthetically difficult in bisphosphonic acids. Therefore, it is an important research progress in the development of a medicament of bisphosphonic acid to explore a synthetic pathway of a series of fluorine-containing bisphosphonate derivatives, synthesize them systematically and study their physiological activities.

DOCUMENT LIST

Non-Patent Documents non-patent document 1: N. Engl. J. Med., 360(7):679-691 Feb. 12, 2009
non-patent document 2: Lancet 376: 1989-1999 2010
non-patent document 3: N. Engl. J. Med., 340(9):737-738 Mar. 4, 1999
non-patent document 4: J. Immunol. 191:1029-1042 2013

SUMMARY OF THE INVENTION

Problems to be Solved by the Invention

The problem of the present invention is to provide a novel fluorine-containing bisphosphonate derivative capable of efficiently inducing proliferation of peripheral blood γδ T cells that express Vγ2Vδ2 T cell receptor having superior cytotoxicity against tumor cells and virus infected cells, immunizing tumor cells and virus infected cells, and inducing cytotoxicity by γδ T cells.

Means of Solving the Problems

The present inventors have conducted intensive studies in an attempt to solve the above-mentioned problem, and found that a series of fluorine-containing bisphosphonic acid having a basic skeleton P—C(F)—P immunize monocytes and can induce proliferation of γδ T cells, and said compound group immunizes tumor cells and virus infected cells and can promote sensitivity of γδ T cells to cytotoxicity, which resulted in the completion of the present invention. To be specific, a series of fluorine-containing bisphosphonic acid in which an alkylamine side chain is added, a series of fluorine-containing bisphosphonic acids in which an amino group substituted by a heterocyclic group or a heterocyclic group containing a nitrogen atom is added, and a series of fluorine-containing bisphosphonate derivatives in which the acid moiety is esterified by an alkoxymethyl group such as pivaloyloxymethyl (POM) group, n-butanoyloxymethyl (BuOM) group and the like were synthesized, and the γδ T cell proliferation-inducing ability and tumor cell and virus infected cell-sensitizing ability of such novel compounds were verified. That is, the present invention is as shown below.

[1] A compound represented by the following formula (I):

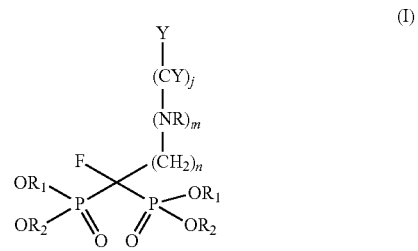

wherein Cy is a phenyl group or a heterocyclic group, Y is a hydrogen atom, an alkyl group, a halogen atom, an alkyl halide group, a hydroxyl group, an aryl group optionally substituted by a halogen atom or an alkoxy group, or an aralkyloxy group, F is a fluorine atom, P is a phosphorus atom, R is a hydrogen atom or an alkyl group, $R_1$ and $R_2$ are the same or different from each other and each is a hydrogen atom or an alkylcarbonyloxyalkyl group, j is a number 0 or 1, m is a number 0 or 1, and n is an integer of 1-6, provided that a compound wherein Cy is a 3-pyridyl group, m is 1, n is 1, Y is a hydrogen atom, and $R_1$ and $R_2$ are hydrogen atoms is excluded, or a pharmaceutically acceptable salt thereof.

[2] The compound of the above-mentioned [1], wherein, in the formula (I), Cy is a phenyl group, or a pharmaceutically acceptable salt thereof.

[3] The compound of the above-mentioned [1], wherein, in the formula (I), Cy is a 5- to 10-membered heterocyclic group containing 1 to 3 atoms selected from a nitrogen atom, a sulfur atom and an oxygen atom, or a pharmaceutically acceptable salt thereof.

[4] The compound of the above-mentioned [1], wherein, in the formula (I), Cy is a 5- or 6-membered heterocyclic group containing 1 or 2 atoms selected from a nitrogen atom and a sulfur atom, or a pharmaceutically acceptable salt thereof.

[5] The compound of the above-mentioned [1], wherein, in the formula (I), Cy is an imidazolyl group, a thiazolyl group, a pyridyl group, a pyrimidyl group, or a 7-azaindolyl group, or a pharmaceutically acceptable salt thereof.

[6] The compound of any of the above-mentioned [1]-[5], wherein, in the formula (I), Y is a hydrogen atom, a $C_{1-3}$ alkyl group, a halogen atom, an alkyl halide group or a phenyl group, and $R_1$ and $R_2$ are the same or different and each is a hydrogen atom or a $C_{2-7}$ alkylcarbonyloxy-$C_{1-3}$ alkyl group, or a pharmaceutically acceptable salt thereof.

[7] The compound of the above-mentioned [1], wherein, in the formula (I), j is 1, Cy is an imidazolyl group, Y is a hydrogen atom or halogen atom, and $R_1$ and $R_2$ are the same or different and each is a hydrogen atom or a $C_{2-7}$ alkylcarbonyloxy-$C_{1-3}$ alkyl group, or a pharmaceutically acceptable salt thereof.

[8] The compound of the above-mentioned [1], wherein, in the formula (I), j is 0, Y is a hydrogen atom or a $C_{1-3}$ alkyl group, and $R_1$ and $R_2$ are the same or different and each is a hydrogen atom or a $C_{2-7}$ alkylcarbonyloxy-$C_{1-3}$ alkyl group, or a pharmaceutically acceptable salt thereof.

[9] The compound of the above-mentioned [1], wherein, in the formula (I), j is 0, Y is a hydrogen atom, R is a hydrogen atom, and $R_1$ and $R_2$ are each a hydrogen atom, or a pharmaceutically acceptable salt thereof.

[10] The compound of the above-mentioned [1], wherein, in the formula (I), j is 0, Y is a $C_{1-3}$ alkyl group, R is a $C_{1-6}$ alkyl group, and $R_1$ and $R_2$ are each a hydrogen atom, or a pharmaceutically acceptable salt thereof.

[11] The compound of the above-mentioned [1], wherein, in the formula (I), j is 1, Cy is an imidazolyl group, Y is a hydrogen atom, and $R_1$ and $R_2$ are the same or different and each is a hydrogen atom or pivaloyloxymethyl (POM) group, or a pharmaceutically acceptable salt thereof.

[12] Any one of compounds represented by the following formulas, or a pharmaceutically acceptable salt thereof:

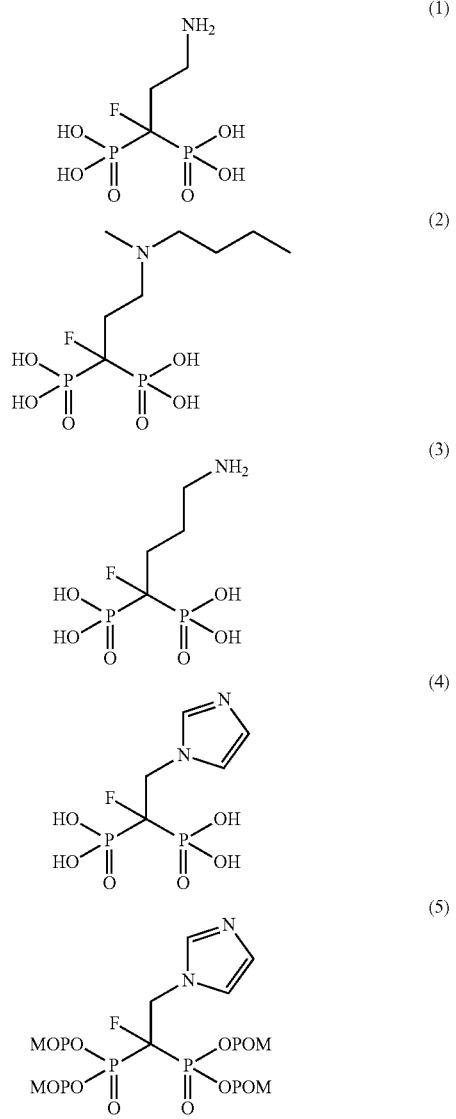

[13] A pharmaceutical composition comprising the compound of any of the above-mentioned [1]-[12], or a pharmaceutically acceptable salt thereof as an active ingredient.

[14] The pharmaceutical composition of the above-mentioned [13], which is an anti-tumor cell agent.

[15] The pharmaceutical composition of the above-mentioned [13], which is an anti-virus-infected cell agent.

[16] The pharmaceutical composition of the above-mentioned [13], which is a lymphocyte-treating agent.

[17] A method of treating a lymphocyte in a living body, comprising administering an effective amount of the compound of any of the above-mentioned [1]-[12], or a pharmaceutically acceptable salt thereof to the body.

[18] A method of proliferating and/or inducing a γδ T cell, comprising administering an effective amount of the compound of any of the above-mentioned [1]-[12], or a pharmaceutically acceptable salt thereof to a living body.

[19] A method of suppressing proliferation of a tumor cell, comprising administering an effective amount of the compound of any of the above-mentioned [1]-[12], or a pharmaceutically acceptable salt thereof to a living body.

[20] A method of treating cancer, comprising administering an effective amount of the compound of any of the above-mentioned [1]-[12], or a pharmaceutically acceptable salt thereof to a living body.

[21] A method of proliferating and/or inducing a γδ T cell, comprising reacting ex vivo the compound of any of the above-mentioned [1]-[12], or a pharmaceutically acceptable salt thereof with a sample containing γδ T cells.

[22] A method of suppressing proliferation of a tumor cell, comprising a step of reacting the compound of any of the above-mentioned [1]-[12], or a pharmaceutically acceptable salt thereof with a sample containing γδ T cells collected from a living body, and a step of returning the γδ T cells to the living body.

In the present specification, a compound represented by the above-mentioned formula (I) is to be also referred to as the compound of the present invention, or the fluorine-containing bisphosphonic acid or fluorine-containing bisphosphonate derivative of the present invention.

Effect of the Invention

When the novel fluorine-containing bisphosphonic acid or fluorine-containing bisphosphonate derivative of the present invention is reacted with peripheral blood mononuclear cells, and cultured together with interleukin-2 (IL-2) for 11 days, not less than 90% of the total cells become Vδ2 positive γδ T cells. The Vδ2 positive γδ T cells induced to proliferate show a cell-injuring activity on various tumor cells and virus infected cells. Furthermore, when tumor cells and virus infected cells are reacted with the novel fluorine-containing bisphosphonic acid or fluorine-containing bisphosphonate derivative of the present invention, the recognition ability of Vδ2 positive γδ T cells is enhanced and the cells become more prone to cytotoxicity. That is, tumor cells and virus infected cells are immunized, and easily injured by Vδ2 positive γδ T cells. Utilizing this property, a novel immunotherapy of cancer and virus infection disease becomes possible.

When the novel fluorine-containing bisphosphonic acid or fluorine-containing bisphosphonate derivative of the present invention is reacted with peripheral blood mononuclear cells, it is selectively incorporated into monocytes having high liquid phase endocytosis ability. The fluorine-containing bisphosphonic acid directly inhibits farnesyl diphosphate synthase, and the fluorine-containing bisphosphonate derivative undergoes hydrolysis of the ester, is converted to bisphosphonic acid and inhibits farnesyl diphosphate synthase. Due to the inhibitory action, isopentenyl diphosphate, which is a metabolite located directly upstream of the enzyme, is intracellularly accumulated. Isopentenyl diphosphate binds to an intracellular region of the butyrophilin 3A1 molecule present in the cellular membrane, and changes the conformation of the extracellular region or changes the degree of polymerization. The change is recognized by Vδ2 positive γδ T cells, and proliferation stimulation is produced. When a cell proliferation factor such as IL-2, IL-15 and the like acts thereon, γδ T cells proliferate markedly. The proliferated γδ T cells show high tumor cell toxicity, and high virus infected cell toxicity.

When the fluorine-containing bisphosphonic acid or fluorine-containing bisphosphonate derivative of the present invention is reacted with tumor cells and virus infected cells, these medicaments are incorporated into the cells, and a phenomenon similar to the changes in the monocytes occurs. That is, the fluorine-containing bisphosphonic acid directly inhibits farnesyl diphosphate synthase, and the fluorine-containing bisphosphonate ester derivative undergoes hydrolysis of the ester, is converted to bisphosphonic acid and inhibits farnesyl diphosphate synthase. Due to the inhibitory action, isopentenyl diphosphate, which is a metabolite located directly upstream of the enzyme, is intracellularly accumulated. Isopentenyl diphosphate binds to an intracellular region of the butyrophilin 3A1 molecule present in the cellular membrane, and changes the conformation of the extracellular region or changes the degree of polymerization. The change is recognized by Vδ2 positive γδ T cells, and tumor cells and virus infected cells are efficiently injured.

Utilizing these actions of the fluorine-containing bisphosphonic acid or fluorine-containing bisphosphonate derivative of the present invention, a novel immunotherapy of cancer and virus infection can be established. This therapy roughly includes two methods. One is an adoptive immunotherapy, and the other is a direct administration method.

In adoptive immunotherapy, mononuclear cells are purified from the peripheral blood of cancer patients or virus infection patients, the fluorine-containing bisphosphonic acid or fluorine-containing bisphosphonate derivative of the present invention is added, IL-2 is further added, and the cells are cultured for 11 days, whereby not less than 90% of the total cells become Vδ2 positive γδ T cells and the proliferation rate becomes not less than 1000-fold. This cell standard product is washed with PBS and intravenously administered to patients. In this case, when the fluorine-containing bisphosphonic acid or fluorine-containing bisphosphonate derivative of the present invention is administered before administration the cell, cancer cells or virus infected cells are immunized and the sensitivity to γδ T cells increases.

In the direct administration method, the fluorine-containing bisphosphonic acid or fluorine-containing bisphosphonate derivative of the present invention is intravenously administered to cancer patients or virus infection patients. In this case, a part of the compound is incorporated into the monocyte by liquid phase endocytosis, the fluorine-containing bisphosphonic acid directly inhibits farnesyl diphosphate synthase, and the fluorine-containing bisphosphonate derivative undergoes hydrolysis of the ester, is converted to bisphosphonic acid and inhibits farnesyl diphosphate synthase. Due to the inhibitory action, isopentenyl diphosphate, which is a metabolite located directly upstream of the enzyme, is intracellularly accumulated, binds to an intracellular region of the butyrophilin 3A1 molecule present in the cellular membrane, and changes the conformation of the extracellular region or changes the degree of polymerization. The change is recognized by Vδ2 positive γδ T cells, and proliferation stimulation occurs. On the other hand, the remaining compound is incorporated into the tumor cells or virus infected cells, induces an action similar to that in the monocyte and promotes sensitivity to γδ T cells. In this way, proliferated γδ T cells efficiently injure tumor cells or virus infected cells and induce antitumor activity and/or antivirus activity.

As mentioned above, the fluorine-containing bisphosphonic acid or fluorine-containing bisphosphonate derivative of the present invention induces proliferation of γδ T cell, which is one kind of immunocyte, and promotes sensitivity of tumor cells and/or virus infected cells to γδ T cells, and therefore, it is utilizable as a low molecule medicament for an antitumor immune cell therapy and an anti viral infection immune therapy.

DESCRIPTION OF EMBODIMENTS

Figure 1:
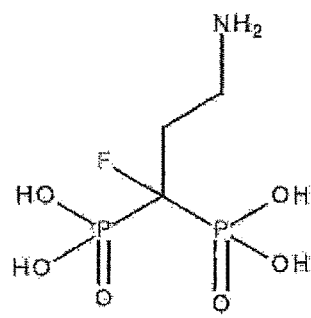
FIG. 1 shows specific examples of the fluorine-containing bisphosphonic acid or fluorine-containing bisphosphonate derivative of the present invention. The numbers indicated in the parentheses in the structural formulas show compound numbers. (1) A compound in which a hydroxyl group bonded to a methylene carbon atom substituted by two phosphorus atoms of pamidronic acid is substituted by a fluorine atom (PAMF). (2) A compound in which a hydroxyl group bonded to a methylene carbon atom substituted by two phosphorus atoms of ibandronic acid is substituted by a fluorine atom (IBAF). (3) A compound in which a hydroxyl group bonded to a methylene carbon atom substituted by two phosphorus atoms of alendronic acid is substituted by a fluorine atom (ALEF). (4) A compound in which a hydroxyl group bonded to a methylene carbon atom substituted by two phosphorus atoms of zoledronic acid is substituted by a fluorine atom (ZOLF). (5) A compound in which a hydroxyl group bonded to a methylene carbon atom substituted by two phosphorus atoms of zoledronic acid is substituted by a fluorine atom, and four OH bonded to the phosphorus atom are substituted by POM groups (ZOLF-POM).
Figure 1:
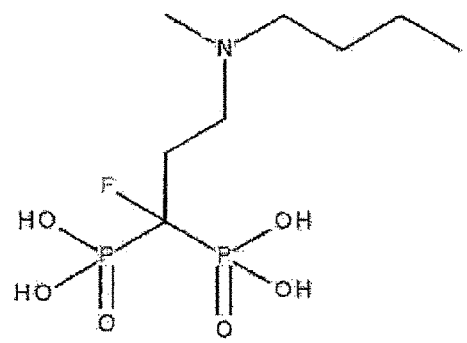
Figure 1:
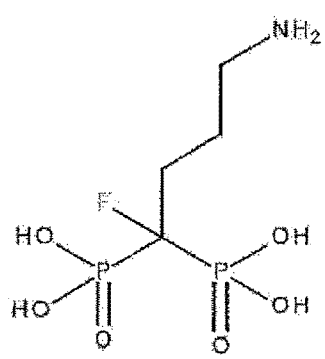
Figure 1:
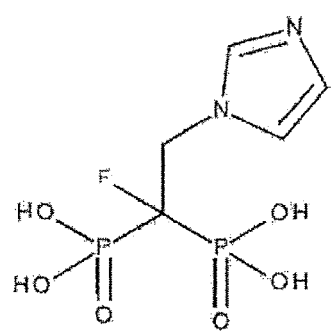
Figure 1:
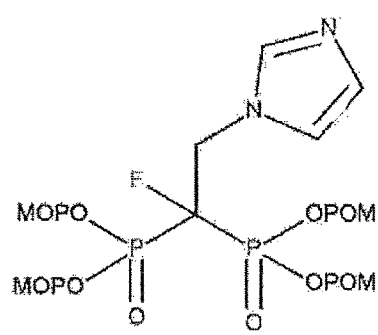

One embodiment of the fluorine-containing bisphosphonic acid or fluorine-containing bisphosphonate derivative to be used in the present invention is represented by the following formula (I):

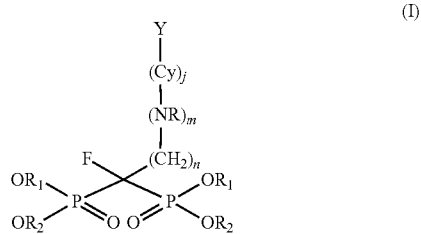

wherein Cy is a phenyl group or a heterocyclic group, Y is a hydrogen atom, an alkyl group, a halogen atom, an alkyl halide group, a hydroxyl group, an aryl group optionally substituted by a halogen atom or an alkoxy group, or an aralkyloxy group, F is a fluorine atom, P is a phosphorus atom, R is a hydrogen atom or an alkyl group, $R_1$ and $R_2$ are the same or different from each other and each is a hydrogen atom or an alkylcarbonyloxyalkyl group, j is a number 0 or 1, m is a number 0 or 1, and n is an integer of 1-6, provided that a compound wherein Cy is a 3-pyridyl group, m is 1, n is 1, Y is a hydrogen atom, and $R_1$ and $R_2$ are hydrogen atoms is excluded.

Cy is a phenyl group or a heterocyclic group, to which at least Y is bonded. The heterocyclic group is a 4- to 15-membered monocyclic heterocyclic group or condensed polycyclic heterocyclic group containing, as a ring-constituting atom besides carbon atom, 1-4 hetero atoms selected from a nitrogen atom, a sulfur atom and an oxygen atom. Examples of the heterocyclic group include furyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl, triazinyl, quinolyl, isoquinolyl, quinazolyl, quinoxalyl, benzofuryl, benzothienyl, benzoxazolyl, benzothiazolyl, benzimidazolyl, benzotriazole, indolyl, indazolyl, pyrrolopyrazinyl, imidazopyridinyl, imidazopyrazinyl, pyrazolopyridinyl, pyazolothienyl, pyrazolotriazinyl, oxetanyl, pyrrolidinyl, piperidinyl, morpholinyl, thiomorpholinyl, piperazinyl, hexamethyleniminyl, oxazolidinyl, thiazolidinyl, imidazolidinyl, oxazolinyl, thiazolinyl, imidazolinyl, dioxolanyl, dihydrooxadiazolyl, pyranyl, tetrahydropyranyl, thiopyranyl, tetrahydrothiopyranyl, tetrahydrofuryl, pyrazolidinyl, pyrazolinyl, tetrahydropyrimidinyl, dihydroindolyl, dihydroisoindolyl, dihydrobenzofuranyl, dihydrobenzodioxinyl, dihydrobenzodioxepinyl, tetrahydrobenzofuranyl, chromenyl, dihydroquinolinyl, tetrahydroquinolinyl, dihydroisoquinolinyl, tetrahydroisoquinolinyl, dihydrophthalazinyl, 7-azaindolyl and the like.

Preferably, the above-mentioned heterocyclic group is a 5- to 10-membered heterocyclic group containing 1-3 hetero atoms selected from a nitrogen atom, a sulfur atom and an oxygen atom, more preferably a 5- or 6-membered heterocyclic group containing 1 or 2 hetero atoms selected from a nitrogen atom and a sulfur atom. Such heterocyclic group is specifically preferably imidazolyl, thiazolyl, pyridyl, pyrimidyl or 7-azaindolyl, more preferably imidazolyl or pyrimidyl, particularly preferably imidazolyl group.

In the above-mentioned heterocyclic group, Y is bonded at a substitutable position. Y is a hydrogen atom, an alkyl group (e.g., $C_{1-10}$ alkyl group such as methyl, ethyl, hexyl, octyl and the like), a halogen atom, (e.g., chlorine atom, fluorine atom, bromine atom), an alkyl halide group (e.g., $C_{1-3}$alkyl group (e.g., methyl, ethyl, propyl) substituted by 1 to 3 halogen atoms (as defined above), a hydroxyl group, an aryl group, or an aralkyloxy group. As used herein, the aforementioned aryl group is optionally substituted by a halogen atom (as defined above) or an alkoxy group (e.g., $C_{1-3}$alkoxy group such as methoxy, ethoxy, propoxy and the like). Preferably, Y is a hydrogen atom, a $C_{1-3}$ alkyl group (as defined above), a halogen atom, an alkyl halide group, an unsubstituted aryl group, more preferably, a hydrogen atom, a methyl group, a halogen atom, a trifluoromethyl group or a phenyl group, most preferably, a hydrogen atom or a bromine atom.

The aryl group encompasses a monocyclic aryl group and a condensed polycyclic aryl group, and specifically, phenyl, biphenyl, naphthyl, anthryl, phenanthryl and acenaphthylenyl can be mentioned. It is preferably a $C_{6-18}$ aryl group, more preferably a $C_{6-8}$ aryl group, particularly preferably a phenyl group.

The aralkyloxy group is preferably a $C_{7-18}$ aralkyloxy group, specifically benzyloxy, phenethyloxy and the like, with preference given to benzyloxy.

$R_1$ and $R_1$ are the same or different from each other and each is a hydrogen atom or an alkylcarbonyloxyalkyl group, and at least one of $R_c$ and $R_2$ is an alkylcarbonyloxyalkyl group. Preferably, both of $R_1$ and $R_2$ are alkylcarbonyloxyalkyl groups. Examples of the alkylcarbonyloxyalkyl group include a $C_{2-7}$ alkylcarbonyloxy-$C_{1-3}$ alkyl group, preferably, $C_{3-4}$ alkylcarbonyloxy-methyl, particularly preferably, pivaloyloxymethyl or n-butanoyloxymethyl.

j is 0 or 1. m is 0 or 1, preferably 1. In the case wherein Cy is secondary amine such as pyrrolyl, pyrrolidinyl, piperidinyl, morpholinyl, thiomorpholinyl, piperazinyl, hexamethyleniminyl, oxazolidinyl, thiazolidinyl, imidazolidinyl and the like, m is 0, Cy is bonded to —$(CH_2)_n$— group at the nitrogen atom. n is an integer of 1-6, preferably 1-3, particularly preferably 1.

The fluorine-containing bisphosphonic acid or fluorine-containing bisphosphonate derivative of the present invention can be efficiently produced by 3 synthesis steps when, for example, a fluorine atom is introduced into bisphosphonic acid (or a derivative thereof). First, (a) a reactive group such as an amino group and the like of bisphosphonic acid to be the starting material is protected, (b) a fluorine atom is introduced by a fluorinating agent, and (c) the protecting group introduced in step a is removed. Examples of the fluorinating agent to be used in step b include N-fluorosulfonimides such as N-fluorophenylsulfonimide, N-fluorotoluenesulfonimide, N-fluoromethanesulfonimide, N-fluorotrifluoromethanesulfonimide and the like, N-fluoropyridinium salts such as N-fluoro-2,4,6-trimethylpyridinium trifluoromethanesulfonate, N-fluoro-2,4,6-trimethylpyridinium tetrafluoroborate and the like, difluoroxenon, fluorine gas and the like. N-fluorosulfonimides are preferable in view of easy availability, easy handling, yield and the like.

Alternatively, when bisphosphonic acid (or a derivative thereof) into which a fluorine atom is introduced is obtainable, the fluorine-containing bisphosphonic acid or fluorine-containing bisphosphonate derivative of the present invention can also be produced by using the compound as a starting material and introducing a desired substituent. The reagent to be used, reaction conditions and the like can be selected and determined by a known method or by appropriately modifying or altering the method according to the kind of the starting material and substituent to be introduced.

The fluorine-containing bisphosphonic acid or fluorine-containing bisphosphonate derivative of the present invention can be specifically synthesized according to the synthesis procedure of the below-mentioned Examples.

The fluorine-containing bisphosphonic acid and fluorine-containing bisphosphonate derivative in the present invention may be pharmaceutically acceptable salts. In addition, when the fluorine-containing bisphosphonic acid and fluorine-containing bisphosphonate derivative of the present invention contain an isomer (e.g., optical isomer, geometric isomer and tautomer) and the like, the present invention encompasses such isomers and also encompasses solvate, hydrate and various shapes of crystals.

In the present invention, as a pharmaceutically acceptable salt, general salts pharmacologically and pharmaceutically acceptable salts can be mentioned. Specific examples of such salt include the following.

Examples of basic addition salt include alkali metal salts such as sodium salt, potassium salt and the like; alkaline earth metal salts such as calcium salt, magnesium salt and the like; ammonium salt; trimethylamine salt, triethylamine salt; aliphaticamine salts such as dicyclohexylamine salt, ethanolamine salt, diethanolamine salt, triethanolamine salt, procaine salt and the like; aralkylamine salts such as N,N-dibenzylethylenediamine and the like; heterocycle aromatic amine salts such as pyridine salt, picoline salt, quinoline salt, isoquinoline salt and the like; quaternary ammonium salts such as tetramethylammonium salt, tetraethylammonium salt, benzyltrimethylammonium salt, benzyltriethylammonium salt, benzyltributylammonium salt, methyltrioctylammonium salt, tetrabutylammonium salt and the like; basic amino acid salts such as arginine salt, lysine salt and the like; and the like.

Examples of acid addition salt include inorganic acid salts such as hydrochloride, sulfate, nitrate, phosphate, carbonate, hydrogencarbonate, perchlorate and the like; organic acid salts such as acetate, propionate, lactate, maleate, fumarate, tartrate, malate, citrate, ascorbate and the like; sulfonates such as methanesulfonate, isethionate, benzenesulfonate, p-toluenesulfonate and the like; acidic amino acid salts such as aspartate, glutamate and the like; and the like.

The novel fluorine-containing bisphosphonic acid and fluorine-containing bisphosphonate derivative of the present invention have a farnesyl diphosphate synthase inhibitory activity. As a result, it suppresses production of isoprenoid metabolites such as cholesterol, liposoluble vitamin, lipoprotein and the like, which are essential for cell survival and exhibits superior direct tumor damaging effect and virus-infected cell cytotoxicity effect. Therefore, the present invention provides direct or indirect antitumor drugs and antiviral agents containing the fluorine-containing bisphosphonic acid and/or a fluorine-containing bisphosphonate derivative as an active ingredient.

The antitumor and antiviral agent of the present invention can be used by administering to the living body, and preferably administered to mammals (human, mouse, rat, hamster, rabbit, cat, dog, bovine, sheep, monkey etc.).

The novel fluorine-containing bisphosphonic acid or fluorine-containing bisphosphonate derivative of the present invention specifically stimulates and proliferates and/or induces Vδ2 positive γδ T cells present in the blood such as peripheral blood in the living body, or lymph fluid, as well as can induce or potentiate an antitumor action of these cells. Therefore, the present invention provides lymphocyte-treating agent containing the fluorine-containing bisphosphonic acid and/or a fluorine-containing bisphosphonate derivative as an active ingredient.

As an antitumor action of the γδ T cells, recognition of a molecule expressing in cancer cells, for example, MICA/B and IPP (isopentenyl pyrophosphate) via a T cell receptor thereof and injury of the cell by γδ T cells can be mentioned. Furthermore, enhancement of antitumor activity by the action of cytokines such as TNF-α, INF-γ and the like produced by γδ T cells can be mentioned.

The lymphocyte-treating agent of the present invention has an action to proliferate and/or induce γδ T cells in vivo and ex vivo. Therefore, the lymphocyte-treating agent of the present invention can be used by treating a sample containing γδ T cells collected from a living body, or directly administering to a living body. Here, the living body means mammals (human, mouse, rat, hamster, rabbit, cat, dog, bovine, sheep, monkey etc.), and human is particularly preferable.

The present invention also includes a method of suppressing proliferation of tumor cells, comprising a step of proliferating and/or inducing γδ T cells by reacting the lymphocyte-treating agent of the present invention on a sample containing γδ T cells collected from a living body, and a step of returning the γδ T cells to the living body.

As a sample containing γδ T cells collected from a living body, blood such as peripheral blood and lymph fluid can be recited as examples. As a target of the lymphocyte-treating agent of the present invention, peripheral blood is preferable, and it is more preferable to use a mononuclear cell fraction separated from the peripheral blood by a specific gravity centrifugation method.

It is possible to stimulate γδ T cells in a sample with the lymphocyte-treating agent of the present invention by culturing the lymphocyte-treating agent and the sample according to a conventional method. It is possible to induce and/or proliferate γδ T cells by culturing in the presence of a fluorine-containing bisphosphonic acid and/or a fluorine-containing bisphosphonate derivative in a trace amount of 100 pM-100 μM, preferably 100 pM-20 μM, further preferably 100 pM-5 μM.

Since the fluorine-containing bisphosphonic acid and a fluorine-containing bisphosphonate derivative as the active ingredient in the lymphocyte-treating agent of the present invention has a bisphosphonic acid skeleton, it shows resistance to alkaliphosphatase as compared to conventional pyrrophosphoric acid lymphocyte-treating agents (Biology Trace Element Research, 104, 131-140 (2005)). Therefore, as a culture medium of γδ T cells to induce and/or proliferate γδ T cells, one containing a serum can be used and, for example, human AB serum, fetal bovine serum and the like can be used. Since a medium containing a serum can be used, γδ T cells can be advantageously provided in an amount sufficient for use in a cancer treatment, conveniently and in a short time.

As a constitution embodiment for use of the lymphocyte-treating agent of the present invention ex vivo for proliferating and/or inducing γδ T cells, the fluorine-containing bisphosphonic acid and/or a fluorine-containing bisphosphonate derivative itself as the active ingredient may be used alone. In addition, it can also be produced as a solution of ethanol, DMSO and the like. Where necessary, other additive can also be added simultaneously. When the lymphocyte-treating agent is reacted with a sample, interleukin-2 (IL-2), interleukin-7 (IL-7), interleukin-15 (IL-15), interleukin-18 (IL-18), and the like may also be added as an aid factor at a concentration of 0.1-150 IU/mL, preferably 1-100 IU/mL or 0.11-1000 ng/mL. Specific induction and/or proliferation of the γδ T cells becomes remarkable by the addition of these.

Induction and/or proliferation of specific γδ T cells by the lymphocyte-treating agent can be evaluated by measuring, after culturing, the IFN-γ amount and/or TNF-α amount produced in the culture supernatant. For example, when the TNF-α production amount is higher than that at the time of start of culture, γδ T cells can be judged to have been induced. The IFN-γ amount and/or TNF-α amount can be performed using a conventionally-known method by using an anti-IFN-γ antibody, an anti-TNF-α antibody and the like.

The γδ T cells treated with the lymphocyte-treating agent of the present invention as mentioned above can be used by administration as a medicament to a patient. For example, a mononuclear cell fraction derived from a patient having a tumor is treated with the lymphocyte-treating agent of the present invention, and a mononuclear cell fraction found to show proliferation and/or induction of γδ T cells is administered as peripheral blood and the like to allow for exhibition of an antitumor activity. As an administration method, methods such as topical injection, intravenous injection, transdermal absorption and the like.

When the antitumor drug, antiviral agent and lymphocyte-treating agent of the present invention are used as pharmaceutical products, they are generally mixed with pharmaceutically acceptable carrier, excipient, diluent, filler, disintegrant, stabilizer, preservative, buffering agent, aromatic, colorant, sweetening agent, thickener, corrigent, solubilizing agents, and other additive known per se, specifically, water, vegetable oil, alcohol (e.g., ethanol, benzyl alcohol etc.), polyethylene glycol, glyceroltriacetate, gelatin, hydrocarbonate (e.g., lactose, starch etc.), magnesium stearate, talc, lanolin, petrolatum and the like, and a tablet, pill, powder, granule, suppository, injection, eye drop, liquid, capsule, troche, aerosol, elixir, suspension, emulsion, syrup and the like are formed by conventional methods, and they can be administered systemically or topically, orally or parenterally.

While the dose varies depending on the age, body weight, symptom, treatment effect, administration method and the like, it is generally 0.001 mg/kg-1000 mg/kg, preferably 0.01 mg/kg-100 mg/kg, per one time in the amount of active ingredient, for an adult, which is administered once to several times per day, orally or in the form of injection such as intravenous injection and the like.

The present invention encompasses direct and indirect antitumor drug and antiviral agent, and shows a treatment effect on benign and malignant tumor, and virus infected cells. In addition, the lymphocyte-treating agent of the present invention is useful for the prophylaxis and/or treatment of tumor. Examples of the tumor target include malignant tumors such as brain tumor (malignant astrocytoma, glioma having oligodendroglial tumor component etc.), esophagus cancer, gastric cancer, liver cancer, pancreatic cancer, large intestine cancer (colorectal cancer, rectal cancer etc.), urinary bladder cancer, lung cancer (non-small cell lung cancer, small cell lung cancer, primary and metastatic squamous cell carcinoma etc.), renal cancer, breast cancer, ovarian cancer, prostate cancer, skin cancer, neuroblastoma, sarcoma, bone and soft tissue tumor, bone tumor, osteosarcoma, testis tumor, extragonadal tumor, orchis tumor, uterine cancer (uterus cervix cancer, uterine body cancer etc.), head and neck tumor (maxilla cancer, laryngeal cancer, pharyngeal cancer, cancer of the tongue, mouth cavity cancer etc.), multiple myeloma, malignant lymphoma (reticulum cell sarcoma, lymphosarcoma, Hodgkin's disease etc.), polycythemia vera, leukemia (acute myeloid leukemia, chronic myeloid leukemia, acute lymphocytic leukemia, chronic lymphocytic leukemia etc.), thyroid cancer, renal pelvis cancer, ureter tumor, bladder tumor, gall bladder cancer, cholangiocarcinoma, choriocarcinoma, malignant melanoma, pediatric tumor (Ewing sarcoma family, Wilms' tumor, rhabdomyosarcoma, blood vessel sarcoma, testicular embryonal carcinoma, neuroblastoma, retinoblastoma, hepatoblastoma, nephroblastoma etc.) and the like and the like. As viral infectious disease to be the target, viral infectious disease such as HTLV-1 infections, HIV infections, influenza disease, herpes disease and the like, and the like can be mentioned. In the present invention, application to urinary bladder cancer, renal cancer, lung cancer, breast cancer, hematologic tumor such as leukemia and the like, and HTLV-1 infections is preferable.

EXAMPLES

The production method of the fluorine-containing bisphosphonic acid and a fluorine-containing bisphosphonate derivative of the present invention is specifically explained below, and shown below. The production method of the compound of the present invention is not limited to those specifically explained below.

Unless specifically indicated, all reactions were performed under air atmosphere. Unless specifically indicated, various reagents used were commercially available products.

(Measurement Method and Marking)

$^1$H NMR, $^{13}$C NMR and $^{19}$F NMR spectra were measured by JNM-AL-400 spectrometer ($^1$H NMR at 400 MHz, $^{13}$C NMR at 100 MHz) and Varian-500PS spectrometer ($^1$H NMR at 500 MHz, $^{13}$C NMR at 125 MHz, $^{19}$F NMR at 470 MHz) (JEOL Ltd., Akishima, Tokyo, Japan) in CDCl$_3$ or D$_2$O solution. $^1$H NMR chemical shift refers to tetramethylsilane (TMS) (0.00 ppm) and $^{13}$C NMR chemical shift refers to CDCl$_3$ (77.0 ppm) and $^{19}$F NMR chemical shift refers to CFCl$_3$. The chemical shift is shown in one-millionth (ppm).

The multiplicity of the peak is abbreviated as follows. s, singlet; d, doublet; dt, doublet of triplets; ddd, doublet of doublet of doublets; dtt, doublet of triplet of triplets; t, triplet; tt, triplet of triplets; q, quartet; m, multiplet; br, broad; pent, pentet Mass spectrum and high resolution mass spectrum were measured by JEOL JMS-T100TD (JEOL Ltd.).

Thin layer chromatography (TLC) was performed on a pre-coated plate (0.25 mm, silica gel plate 60F$_{245}$, Merck Millipore, Mass.).

Column chromatography was performed on a silica gel plate (Kanto Chemical Co., Inc.).

LIST OF ABBREVIATIONS

Me: methyl,
Et: ethyl,
iPr: isopropyl,
Boc: t-butoxycarbonyl,
Boc$_2$O: di-tert-butyl dicarbonate, Et₃N: triethylamine,
CH₂Cl₂: dichloromethane,
quant.: quantitatively obtained,
NFSI: N-fluorobenzenesulfonimide,
n-BuLi: n-butyllithium,
THF: tetrahydrofuran,
HCl: hydrochloric acid,
NaH: sodium hydride,
15-crown-5-ether: 15-crown-5-ether,
MeOH: methanol,
Ms: methanesulfonyl,
MsCl: methanesulfonyl chloride,
K₂CO₃: potassium carbonate,
DMF: N,N-dimethylformamide,
KH: potassium hydride,
18-crown-6-ether: 18-crown-6-ether,
select fluor: 1-chloromethyl-4-fluoro-1,4-diazoniabicyclo[2.2.2]octane bis(tetrafluoroboric acid)

Example 1

Synthesis of 3-amino-1-fluoro-propylidene-1,1-bisphosphonic acid (PAMF)

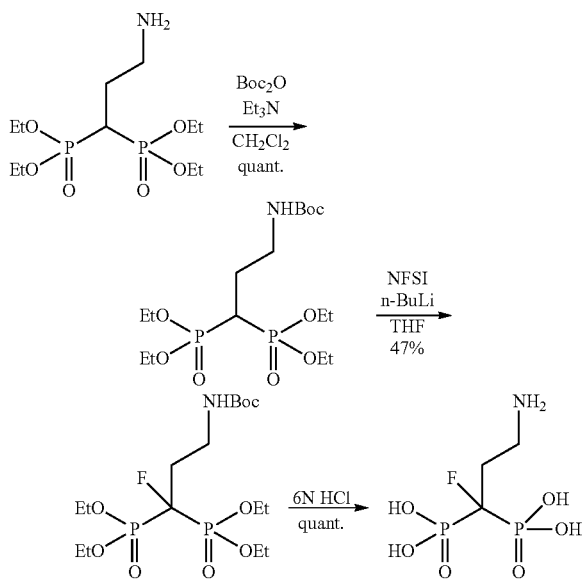

(1) tert-butyl(3,3-bis(diethoxyphosphoryl)propyl)carbamate

Tetraethyl-3-aminopropylidene-1,1-bisphosphonate[1] (460 mg, 1.5 mmol) dissolved in dichloromethane (20 mL) was reacted with Boc₂O (334 μL, 1.5 mmol) and triethylamine (205 μL, 1.5 mmol) at room temperature. The reaction mixture was stirred for 9 hr, the solvent was removed under reduced pressure, and the solution was concentrated. As a result, colorless oily tert-butyl(3,3-bis(diethoxyphosphoryl)propyl)carbamate (575 mg, yield 99%) was obtained.

[1] K. Ogawa, T. Mukai, Y. Arano, H. Hanaoka, K. Hashimot, H. Nishimura, H. Saji, J. Label. Compd Radiopharm. 2004, 47, 753-761.

$^1$H NMR (500 MHz, CDCl₃) δ 1.35 (t, J=7.1 Hz, 6H), 1.53 (s, 9H), 2.06-2.15 (m, 2H), 2.40 (tt, J=6.4, 23.9 Hz, 2H), 3.30-3.37 (m, 2H), 4.17-4.22 (m, 8H), 5.06 (br. s, NH);
$^{13}$C NMR (125 MHz, CDCl₃) δ 16.3-16.3 (m), 27.3, 28.3, 62.6-62.7 (m), 85.1, 146.6;
HRMS (ESI) m/z Calcd for C₁₆H₃₅NNaO₈P₂ [M]⁺ 454.1736, found 454.1696.

(2) tert-butyl(3,3-bis(diethoxyphosphoryl)-3-fluoropropyl)carbamate

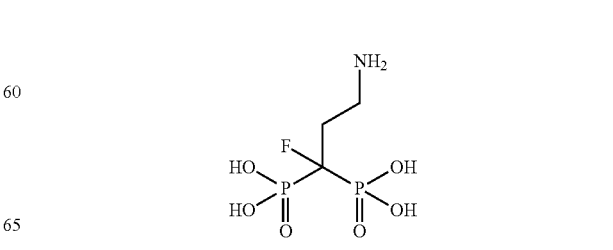

To tert-butyl(3,3-bis(diethoxyphosphoryl)propyl)carbamate (50 mg, 0.13 mmol) dissolved in THF (2.0 mL) was added dropwise n-BuLi (90 μL, 1.6 M hexane solution, 0.14 mmol) at −78° C. under an argon atmosphere. After stirring for 10 min, N-fluorophenylsulfonimide (45 mg, 0.14 mmol) was added to the carbanion solution. The reaction mixture was allowed to reach room temperature over 1 hr. After stirring for 7 hr, the reaction was discontinued with saturated ammonium chloride (10 mL). The reaction product was extracted from the aqueous phase with ethyl acetate (2×10 mL), and the obtained organic phases were mixed. This was dehydrated over magnesium sulfate, and concentrated under reduced pressure. The reaction product was passed through a silica gel column by using acetone/n-hexane=1/1 solvent system. However, since the object product could not be obtained with high purity, 28 mg of a crude product containing tert-butyl(3,3-bis(diethoxyphosphoryl)-3-fluoropropyl)carbamate as the main component was used without further purification for the next reaction.

$^1$H NMR (400 MHz, CDCl₃) δ 1.36 (t, J=8.8 Hz, 12H), 1.42 (s, 9H), 2.33-2.43 (m, 2H), 3.45-3.48 (m, 2H), 4.22-4.31 (m, 8H), 5.18 (br. s, NH).
HRMS (ESI) m/z Calcd for C₁₆H₃₄FNNaO₈P₂ [M]⁺ 472.1641, found 472.1646.

(3) 3-amino-1-fluoro-propylidene-1,1-bisphosphonic acid tert-Butyl(3,3-bis(diethoxyphosphoryl)-3-fluoropropyl)carbamate (28 mg, 0.06 mmol) was dissolved in 1 mL of 6N hydrochloric acid, and the mixture was heated under reflux for 7 hr. The solvent was removed under reduced pressure and the reaction mixture was concentrated. The residue was recrystallized from water/methanol to give a yellow solid (14 mg, yield 45%).

$^1$H NMR (500 MHz, D$_2$O) δ 2.38-2.51 (m, 2H), 3.28-3.34 (m, 2H);

$^{19}$F NMR (470 MHz, D$_2$O) δ −183.4 (tt, J=23.1, 69.2 Hz);

HRMS (ESI) m/z Calcd for C$_3$H$_9$FNO$_6$P$_2$ [M]$^-$ 235.9889, found 235.9852.

Example 2

Synthesis of 1-fluoro-3-(methyl(pentyl)amino)propylidene-1,1-bisphosphonic acid (IBAF)

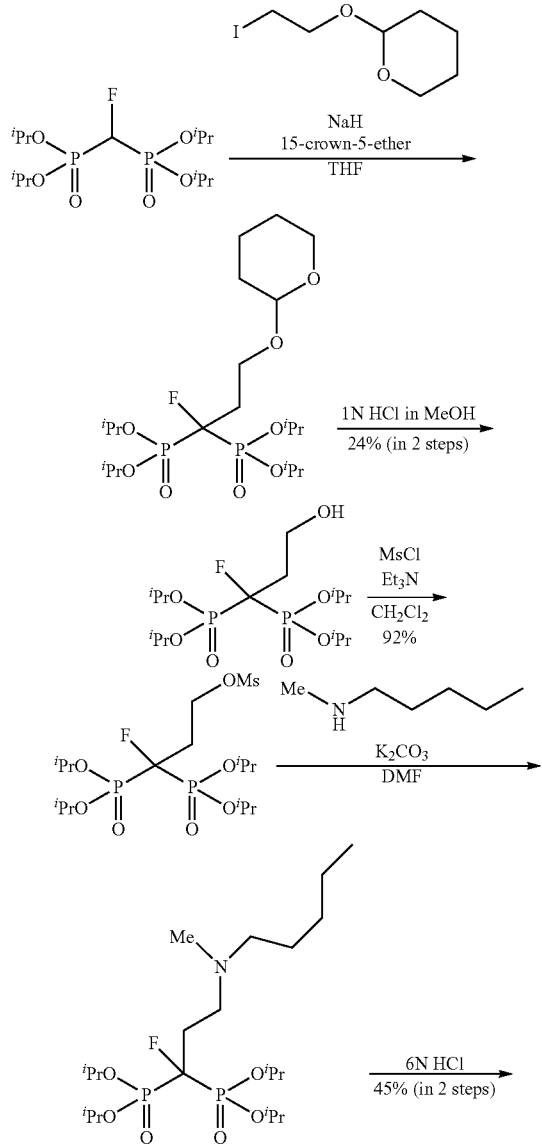

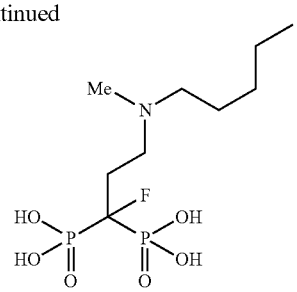

(1) tetraisopropylmonofluoromethylenediphosphonate[2]

[2]V. Jo Davisson, Darrell R. Davis, Vyas M. Dixit, C. Dale Poulter, J. Org. Chem. 1987, 52, 1794-1801.

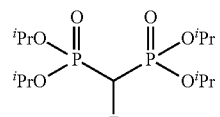

Tetraisopropyl methylenediphosphonate (2.5 g, 7.3 mmol) dissolved in 20 mL of DMF was cooled on ice to 0° C. NaH (386 mg, 60% in mineral oil, 16.6 mmol) dissolved in 20 mL of DMF was placed in a different flask, and cooled for 5 min at 0° C. This NaH solution was added dropwise to tetraisopropyl methylenediphosphonate. The reaction mixture was stirred at 0° C. for 10 min, and allowed to warm to room temperature. After stirring for 1 hr at room temperature, selectfluor (5.7 g, 16.6 mmol) dissolved in DMF was added, and the reaction mixture was stirred for 6 hr at room temperature. This was diluted with 50 mL of dichloromethane, and 50 mL of saturated ammonium chloride solution was added to discontinue the reaction. The aqueous phase was extracted with dichloromethane (2×50 mL) and the obtained organic phase was dried over magnesium sulfate. After filtration, the filtrate was concentrated under reduced pressure, and purified by silica gel column (eluent: gradient of ethyl acetate/n-hexane=1/2 to ethyl acetate 100%) to give monofluoro bisphosphonate (746 mg, yield 22%) and difluorobisphosphonic acid (615 mg, yield 28%).

(2) tetraisopropyl-1-fluoro-3-hydroxypropylidene-1,1-bisphosphonate

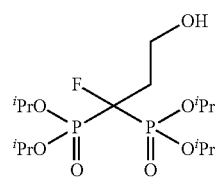 [SMILES: CC(C)OP(=O)(OC(C)C)C(F)(CCO)P(=O)(OC(C)C)OC(C)C]

To a suspension of NaH (96 mg, 60%, 2.4 mmol) in THF (15 mL) prepared under an argon atmosphere was added at 0° C. tetraisopropylmonofluoromethylenediphosphonate (724 mg, 2.0 mmol) dissolved in 5 mL of THF. After stirring for 30 min, 2-(2-iodoethoxy)tetrahydro-2H-pyran (615 mg, 2.4 mmol) and 15-crown-5-ether (88 mg, 0.4 mmol) dissolved in 2 mL of THF was added. The reaction mixture was stirred at room temperature for 24 hr, and the reaction was discontinued with saturated ammonium chloride solution. A compound was extracted from the aqueous phase with ethyl acetate (2×50 mL), and the obtained organic phases were mixed, dehydrated over magnesium sulfate. After filtration, the filtrate was concentrated under reduced pressure. A crude product of tetraisopropyl-1-fluoro-3-((tetrahydro-2H-pyran-2-yl)oxy)propylidene-1,1-bisphosphonate was treated with 2 mL of 1N hydrogen chloride methanol solution, and the mixture was stirred for 10 min. The reaction mixture was concentrated under reduced pressure and purified by silica gel column (eluate: acetone/n-hexane=1/1) to give tetraisopropyl-1-fluoro-3-hydroxypropylidene-1,1-bisphosphonate as a colorless oil (198 mg, yield 24%).

$^1$H NMR (500 MHz, CDCl$_3$) δ 1.37-1.38 (m, 24 H), 2.42 (dtt, J=5.4, 15.2, 27.5 Hz, 2H), 3.88 (t, J=5.1 Hz, 2H), 4.11 (br. s, OH), 4.89-4.90 (m, 4H);

$^{13}$C NMR (125 MHz, CDCl$_3$) δ 23.7-23.8 (m), 24.2-24.3 (m), 36.8 (d, J=19.2 Hz), 73.1 (t, J=3.7 Hz), 73.2 (t, J=3.5 Hz);

$^{19}$F NMR (470 MHz, CDCl$_3$) δ -193.8 (tt, J=22.7, 78.0 Hz);

HRMS (ESI) m/z Calcd for C$_{15}$H$_{33}$FN$_2$NaO$_7$P$_2$ [M]$^+$ 429.1583, found 429.1543.

(3) 2,2-bis(diisopropyloxyphosphoryl)2-fluoroethyl-methanesulfonate

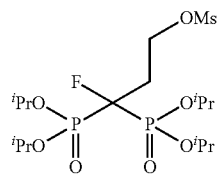 [SMILES: CC(C)OP(=O)(OC(C)C)C(F)(CCOS(C)(=O)=O)P(=O)(OC(C)C)OC(C)C]

To tetraisopropyl-1-fluoro-3-hydroxypropylidene-1,1-bisphosphonate (190 mg, 0.47 mmol) dissolved in 5 mL of dichloromethane were added triethylamine (78 μL, 0.56 mmol) and methanesulfonyl chloride (43 μL, 0.56 mmol) at room temperature. The reaction mixture was stirred for 7 hr, and extracted with ethyl acetate (2×50 mL). The obtained organic phase was washed with water. Then, it was washed with salt water, dehydrated over magnesium sulfate. After filtration, the filtrate was concentrated under reduced pressure and purified by silica gel column (solvent: acetone/n-hexane=1/1) to give 2,2-bis(diisopropyloxyphosphoryl)2-fluoroethylmethanesulfonate (209 mg, yield 92%) as a yellow oil.

$^1$H NMR (500 MHz, CDCl$_3$) δ 1.36-1.38 (m, 24H), 2.53-2.66 (m, 2H), 3.01 (s, 3H), 4.54 (t, J=7.8 Hz, 2H), 4.82-4.91 (m, 4H);

$^{13}$C NMR (125 MHz, CDCl$_3$) δ 23.7 (dt, J=2.8, 12.9 Hz), 24.2 (d, J=28.6 Hz), 32.9 (d, J=20.1 Hz), 37.3, 65.3 (q, J=6.9 Hz), 73.2 (t, J=3.7 Hz), 73.5 (t, J=3.7 Hz);

$^{19}$F NMR (470 MHz, CDCl$_3$) δ -195.0 (tt, J=23.1, 75.1 Hz);

HRMS (ESI) m/z Calcd for C$_{16}$H$_{35}$FNaO$_9$P$_2$S [M]$^+$ 507.1359, found 507.1353.

(4) tetraisopropyl-1-fluoro-3-(methyl(pentyl)amino)propylidene-1,1-bisphosphonate

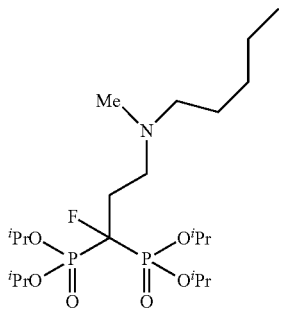 [SMILES: CCCCCN(C)CCC(F)(P(=O)(OC(C)C)OC(C)C)P(=O)(OC(C)C)OC(C)C]

To 2,2-bis(diisopropyloxyphosphoryl)2-fluoroethylmethanesulfonate (150 mg, 0.31 mmol) dissolved in 2.5 mL of DMF was added a solution of potassium carbonate (129 mg, 0.93 mmol) and N-hexylmethylamine (63 mg, 0.62 mmol). The reaction mixture was stirred at 80° C. for 19 hr, and water was added to discontinue the reaction. A compound was extracted from the aqueous phase with ethyl acetate (2×50 mL), and the obtained organic phase was washed with salt water, dehydrated over magnesium sulfate. After filtration, the filtrate was concentrated under reduced pressure and purified by silica gel column chromatography (solvent: acetone/n-hexane=1/1) to give tetraisopropyl-1-fluoro-3-(methyl(pentyl)amino)propylidene-1,1-bisphosphonate (31 mg, yield 21%) as a colorless oily substance.

$^1$H NMR (500 MHz, CDCl$_3$) δ 0.90 (t, J=7.4 Hz, 3H), 1.27-1.39 (m, 28H), 1.44-1.52 (m, 2H), 2.23-2.40 (m, 7 H), 2.72-2.78 (m, 2H), 4.83-4.94 (m, 4H);

$^{13}$C NMR (125 MHz, CDCl$_3$) δ 14.0, 22.6, 23.7 (dt, J=3.0, 18.0 Hz), 24.3, (dt, J=1.4, 32.6 Hz), 27.0, 29.7, 30.3 (d, J=19.1 Hz), 42.0, 50.9 (q, J=6.2 Hz), 57.3, 72.6 (t, J=3.5 Hz), 72.9 (t, J=3.7 Hz);

$^{19}$F NMR (470 MHz, CDCl$_3$) δ -193.6 (tt, J=23.4, 76.2 Hz);

HRMS (ESI) m/z Calcd for C$_{21}$H$_{46}$FNNaO$_6$P$_2$ [M]$^+$ 512.2682, found 512.2686.

(5) 1-fluoro-3-(methyl(pentyl)amino)propylidene-1,1-bisphosphonic acid

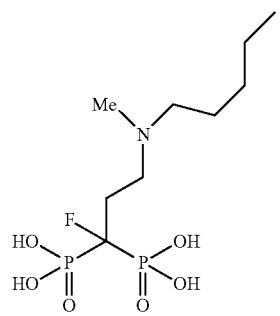 [SMILES: CCCCCN(C)CCC(F)(P(=O)(O)O)P(=O)(O)O]

Tetraisopropyl-1-fluoro-3-(methyl(pentyl)amino)propylidene-1,1-bisphosphonate (30 mg, 0.06 mmol) was dissolved in 1 mL of 6N hydrochloric acid, and heated under reflux for 7 hr. The reaction mixture was concentrated under reduced pressure to give 1-fluoro-3-(methyl(pentyl)amino) propylidene-1,1-bisphosphonic acid (20 mg, yield 99%) as a viscous oil.

$^1$H NMR (500 MHz, D$_2$O) δ 0.79 (t, J=7.1 Hz, 3H), 1.21-1.29 (m, 4H), 1.57-1.72 (m, 2H), 2.42-2.53 (m, 2H), 2.79 (s, 3H), 2.99-3.04 (m, 1H), 3.11-3.17 (m, 1H), 3.26-3.33 (m, 1H), 3.46 (m, 1H);

$^{13}$C NMR (125 MHz, D$_2$O) δ 12.9, 21.4, 23.1, 27.3 (d, J=19.9 Hz), 27.7, 39.4, 51.5-51.7 (m), 56.3;

$^{19}$F NMR (470 MHz, D$_2$O) δ −189.5 (tt, J=21.6, 69.9 Hz);

HRMS (ESI) m/z Calcd for C$_9$H$_{21}$FNNaO$_6$P$_2$ [M]$^-$ 320.0828, found 320.0843.

Example 3

Synthesis of
4-amino-1-fluoro-butylidene-1,1-bisphosphonic acid
(ALEF)

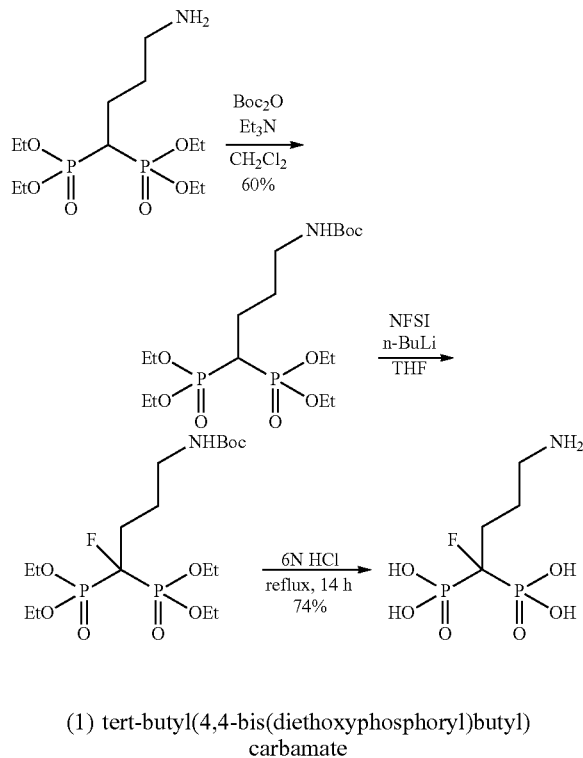

To tetraethyl-4-aminobutylidene-1,1-bisphosphonate (345 mg, 1.0 mmol) dissolved in 10 mL of dichloromethane were added Boc$_2$O (218 μL, 1.0 mmol) and Et$_3$N (139 μL, 1.0 mmol) at room temperature. The reaction mixture was stirred for 20 hr, the solvent was removed under reduced pressure, and the solution was concentrated. The crude product was purified by silica gel column chromatography using acetone as a solvent to give tert-butyl(4,4-bis(diethoxyphosphoryl)butyl)carbamate (267 mg, yield 60%) as a colorless oil.

$^1$H NMR (500 MHz, CDCl$_3$) δ 1.29 (t, J=7.1 Hz, 12 H), 1.38 (s, 9H), 1.71 (pent, J=7.1 Hz, 2H), 1.85-1.96 (m, 2H), 2.24 (tt, J=5.9, 23.9 Hz, 2H), 3.02-3.13 (m, 2H), 4.08-4.16 (m, 8H), 4.76 (br. s, NH);

$^{13}$C NMR (125 MHz, CDCl$_3$) δ 16.2 (d, J=2.8 Hz), 16.9 (d, J=2.5 Hz), 22.6 (t, J=5.1 Hz), 28.3, 28.9 (m), 30.1 (t, J=132.6 Hz), 39.7, 62.4 (d, J=6.5 Hz), 62.5 (d, J=6.7 Hz), 78.8, 155.8;

HRMS (ESI) m/z Calcd for C$_{17}$H$_{37}$NNaO$_8$P$_2$ [M]$^+$ 468.1892, found 468.1868.

(2) tert-butyl(4,4-bis(diethoxyphosphoryl)-4-fluorobutyl)carbamate

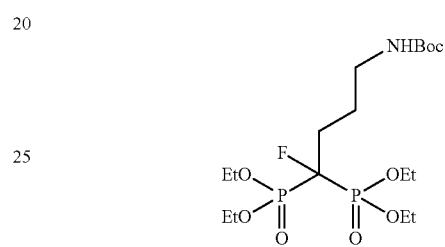

To tert-butyl(4,4-bis(diethoxyphosphoryl)butyl)carbamate (220 mg, 0.49 mmol) dissolved in 12 mL of THF was added dropwise n-BuLi (338 μL, 1.6 M hexane solution, 0.54 mmol) at −78° C. under an argon atmosphere. After stirring for 10 min, N-fluorophenylsulfonimide was added to carbanion solution and the mixture was allowed to warm to room temperature over 1 hr. After stirring for 12 hr, the reaction was discontinued by adding 10 mL of ammonium chloride solution. A compound was extracted from the aqueous phase with ethyl acetate (2×10 mL), and the organic phase was blended, dehydrated over magnesium sulfate. After filtration, the filtrate was concentrated under reduced pressure and crudely purified by silica gel column chromatography (solvent: acetone/ethyl acetate=1/1). The crude product containing tert-butyl(4,4-bis(diethoxyphosphoryl)-4-fluorobutyl)carbamate as the main component was directly used in the next synthesis reaction (184 mg, yield <82%).

$^1$H NMR (500 MHz, CDCl$_3$) δ 1.36 (t, J=7.1 Hz, 12H), 1.43 (s, 9H), 1.82-1.88 (m, 2H), 2.12-2.26 (m, 2H), 3.09-3.20 (m, 2H), 4.20-4.33 (m, 8H), 4.62 (br. s, NH);

HRMS (ESI) m/z Calcd for C$_{17}$H$_{36}$FNNaO$_8$P$_2$ [M]$^+$ 486.1798, found 486.1811.

(3) 4-amino-1-fluoro-butylidene-1,1-bisphosphonic acid

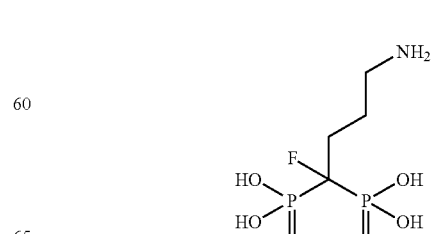

tert-Butyl (4,4-bis(diethoxyphosphoryl)-4-fluorobutyl) carbamate (100 mg, 0.22 mmol) was dissolved in 2 mL of 6N hydrochloric acid, and heated under reflux for 15 hr. The reaction mixture was concentrated under reduced pressure, whereby the solvent was removed. The residue was recrystallized from water/methanol to give 4-amino-1-fluoro-butylidene-1,1-bisphosphonic acid (15 mg, yield 74%) as a white solid.

$^1$H NMR (500 MHz, D$_2$O) δ 1.93-2.04 (m, 2H), 2.08-2.23 (m, 2H), 2.95-3.05 (m, 2H);

$^{13}$C NMR (125 MHz, D$_2$O) δ 21.7 (q, J=6.0 Hz), 29.3 (d, J=19.6 Hz), 39.5;

$^{19}$F NMR (470 MHz, D$_2$O) δ −189.5 (tt, J=23.8, 72.5 Hz);

HRMS (ESI) m/z Calcd for C$_9$H$_{19}$FNO$_8$P$_2$ [M]$^-$ 250.0046, found 250.0069.

Example 4

Synthesis of 1-fluoro-(2-imidazoyl-1-ethylidene)-1,1-bisphosphonic acid (ZOLF)

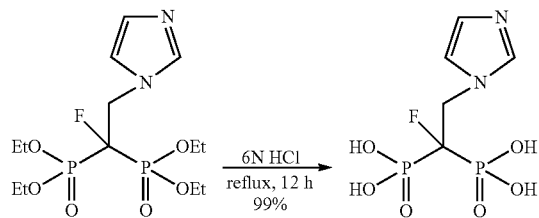

Tetrakisisopropyl-1-fluoro-(2-imidazoyl-1-ethylidene)-1,1-bisphosphonate (58 mg, 0.15 mmol) was dissolved in 1 mL of 6N hydrochloric acid, and heated under reflux for 12 hr. The reaction mixture was concentrated under reduced pressure, whereby the solvent was removed. The residue was recrystallized from water/methanol to give 1-fluoro-(2-imidazoyl-1-ethylidene)-1,1-bisphosphonic acid (42 mg, yield 99%) as a white solid.

$^1$H NMR (500 MHz, D$_2$O) δ 4.72-4.81 (m, 2H), 7.28 (s, 1H), 7.37 (s, 1H), 8.62 (s, 1H);

$^{13}$C NMR (125 MHz, D$_2$O) δ 51.2 (br. d, J=18.5 Hz), 118.7, 123.6, 135.9;

$^{19}$F NMR (470 MHz, D$_2$O) δ −189.8 (tt, J=25.7, 67.9 Hz, 1F);

HRMS (ESI) m/z Calcd for C$_5$H$_8$FN$_2$O$_6$P$_2$ [M]$^-$ 272.9842, found 272.9807.

Example 5

Synthesis of tetrakispivaloyloxymethyl-1-fluoro-2-(1H-imidazoyl-1-ethylidene)-1,1-bisphosphonate (ZOLF-POM)

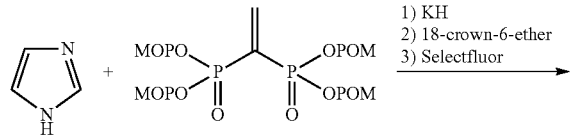

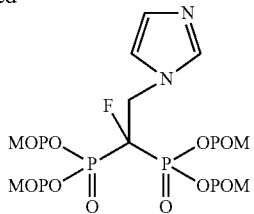

To potassium hydride (21 mg, 30%, 0.16 mmol) suspended in 2 mL of THF was added imidazole (11 mg, 0.16 mmol) at 0° C. under an argon atmosphere. After stirring at 0° C. for 1 hr, the mixture was stirred at room temperature for 30 min. This was cooled to 0° C., and 1.5 mL of a solution of tetrakispivaloyloxymethylvinylidene-1,1-bisphosphonate (100 mg, 0.16 mmol) in THF was added. This was stirred for 30 min, and 1.5 mL of a solution of 18-crown-6-ether (8.2 mg, 0.03 mmol) in THF was added. The reaction mixture was stirred for 15 min and selectfluor (82 mg, 0.23 mmol) was added. The reaction mixture was stirred for 17 hr, and the reaction was discontinued with 5 mL of aqueous ammonium chloride solution. A compound was extracted from the aqueous phase with ethyl acetate (2×10 mL), and the organic phase was mixed, dehydrated over magnesium sulfate. After filtration, the filtrate was concentrated under reduced pressure and purified by silica gel column chromatography (eluent: acetone/n-hexane=1/1 to acetone/methanol=10/1). As a result, tetrakispivaloyloxymethyl-1-fluoro-2-(1H-imidazoyl-1-ethylidene)-1,1-bisphosphonate was obtained (30 mg, yield 26%).

$^1$H NMR (500 MHz, CDCl$_3$) δ 1.23 (s, 36H), 4.67 (ddd, J=9.1, 10.3, 25.9 Hz, 2H), 5.60-5.71 (m, 8H), 6.96 (s, 1H), 7.02 (s, 1H), 7.51 (s, 1H);

$^{13}$C NMR (125 MHz, CDCl$_3$) δ 26.8, 26.8, 38.7, 28.7, 48.1 (m), 82.8 (dt, J=3.2, 70.2 Hz), 120.7 (d, J=1.6 Hz), 129.2, 138.5 (d, J=1.2 Hz), 176.5, 176.6;

$^{19}$F NMR (470 MHz, CDCl$_3$) δ −191.6 (tt, J=26.0, 71.8 Hz);

HRMS (ESI) m/z Calcd for C$_{29}$H$_{49}$FN$_2$NaO$_{14}$P$_2$ [M]$^+$ 753.2541, found 753.2502.

Methods using the fluorine-containing bisphosphonic acid or fluorine-containing bisphosphonate derivative of the present invention as a lymphocyte-treating agent are specifically explained in Experimental Examples 1-5. The lymphocyte treatment method using the compound of the present invention is not limited to those specifically explained in the following.

The peripheral blood derived from each patient and used in the Experimental Examples was obtained from the patients hospitalized in the Nagasaki University Hospital and approved by the Nagasaki University Hospital clinical Research Ethics Committee.

Figure 2:
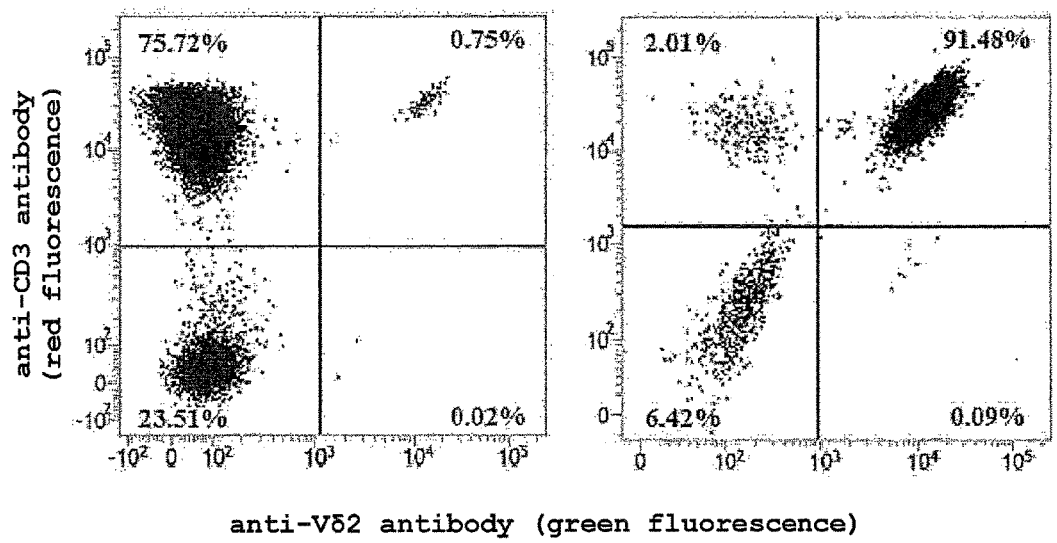
FIG. 2 shows the results of FACS analysis of peripheral blood mononuclear cells of adult T cell leukemia patient (1) which were stained with phycoerythrin (PE)-labeled anti-human CD3 antibody and fluorescein isothiocyanate (FITC)-labeled anti-human Vδ2 antibody (left Figure). The results of FACS analysis of peripheral blood mononuclear cells of adult T cell leukemia patient (1) which were reacted with ZOLF-POM, cultured for 11 days together with IL-2, and stained with PE-labeled anti-human CD3 antibody and FITC labeled anti-human Vδ2 antibody (right Figure).

Experimental Example 1 (FIG. 2)

Heparin blood samples (peripheral blood 10 mL) were collected from adult T cell leukemia patients (1), and diluted with 10 mL of PBS. This was overlaid on 20 mL of Ficoll-Paque and subjected to density gradient centrifugation at 600×g for 30 min at room temperature. The layer directly above Ficoll-Paque was recovered, and washed 3 times with PBS to give peripheral blood mononuclear cells. The cells were suspended in 7 mL of Yssel medium, 1 mL therefrom was stained with PE-labeled anti-human CD3 monoclonal antibody and FITC-labeled anti-human Vδ2 monoclonal antibody, and analyzed by flow cytometer. As a result, as shown in the panel on the left side in FIG. 2, Vδ2 positive γδ T cells accounted for 0.75% of lymphocyte gate. The peripheral blood mononuclear cells suspended in Yssel medium were reacted with ZOLF-POM (1 μM), cultured for 11 days together with IL-2, stained with PE-labeled anti-human CD3 monoclonal antibody and FITC-labeled anti-human Vδ2 monoclonal antibody, and analyzed by flow cytometer. As a result, as shown in the panel on the right side in FIG. 2, Vδ2 positive γδ T cells accounted for 91.48% of lymphocyte gate. This shows that Vδ2 positive γδ T cells with high purity can be easily prepared in a large amount in 11 days from the peripheral blood mononuclear cells of adult T cell leukemia patients by using ZOLF-POM.

Figure 3:
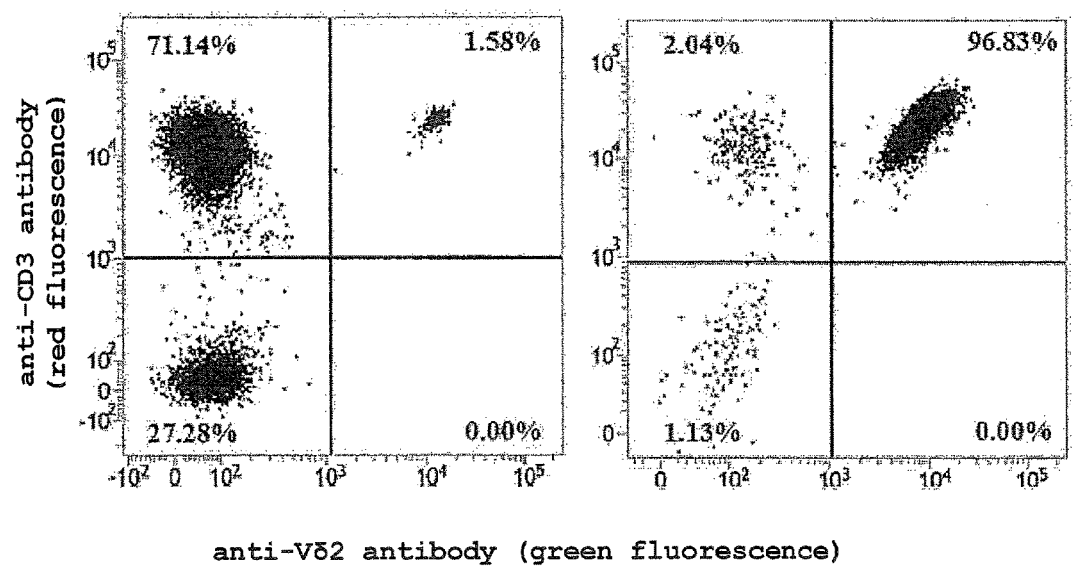
FIG. 3 shows the results of FACS analysis of peripheral blood mononuclear cells of adult T cell leukemia patient (2) which were stained with PE-labeled anti-human CD3 antibody and FITC-labeled anti-human Vδ2 antibody (left Figure). The results of FACS analysis of peripheral blood mononuclear cells of adult T cell leukemia patient (2) which were reacted with ZOLF-POM, cultured for 11 days together with IL-2, and stained with PE-labeled anti-human CD3 antibody and FITC labeled anti-human Vδ2 antibody (right Figure).

Experimental Example 2 (FIG. 3)

Heparin blood samples (peripheral blood 10 mL) were collected from adult T cell leukemia patients (2), and diluted with 10 mL of PBS. This was overlaid on 20 mL of Ficoll-Paque and subjected to density gradient centrifugation at 600×g for 30 min at room temperature. The layer directly above Ficoll-Paque was recovered, and washed 3 times with PBS to give peripheral blood mononuclear cells. The cells were suspended in 7 mL of Yssel medium, 1 mL therefrom was stained with PE-labeled anti-human CD3 monoclonal antibody and FITC-labeled anti-human Vδ2 monoclonal antibody, and analyzed by flow cytometer. As a result, as shown in the panel on the left side in FIG. 3, Vδ2 positive γδ T cells accounted for 1.58% of lymphocyte gate. The peripheral blood mononuclear cells suspended in Yssel medium were reacted with ZOLF-POM (1 μM), cultured for 11 days together with IL-2, stained with PE-labeled anti-human CD3 monoclonal antibody and FITC-labeled anti-human Vδ2 monoclonal antibody, and analyzed by flow cytometer. As a result, as shown in the panel on the right side in FIG. 3, Vδ2 positive γδ T cells accounted for 96.83% of lymphocyte gate. This shows that Vδ2 positive γδ T cells with high purity can be easily prepared in a large amount in 11 days from the peripheral blood mononuclear cells of adult T cell leukemia patients by using ZOLF-POM.

Figure 4:
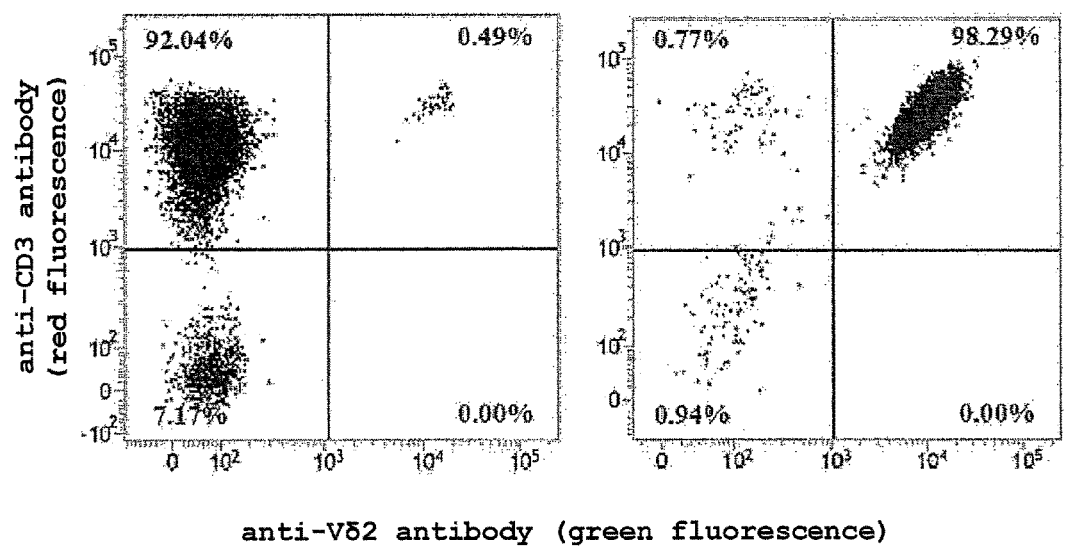
FIG. 4 shows the results of FACS analysis of peripheral blood mononuclear cells of adult T cell leukemia patient (3) which were stained with PE-labeled anti-human CD3 antibody and FITC-labeled anti-human Vδ2 antibody (left Figure). The results of FACS analysis of peripheral blood mononuclear cells of adult T cell leukemia patient (3) which were reacted with ZOLF-POM, cultured for 11 days together with IL-2, and stained with PE-labeled anti-human CD3 antibody and FITC labeled anti-human Vδ2 antibody (right Figure).

Experimental Example 3 (FIG. 4)

Heparin blood samples (peripheral blood 10 mL) were collected from adult T cell leukemia patients (3), and diluted with 10 mL of PBS. This was overlaid on 20 mL of Ficoll-Paque and subjected to density gradient centrifugation at 600×g for 30 min at room temperature. The layer directly above Ficoll-Paque was recovered, and washed 3 times with PBS to give peripheral blood mononuclear cells. The cells were suspended in 7 mL of Yssel medium, 1 mL therefrom was stained with PE-labeled anti-human CD3 monoclonal antibody and FITC-labeled anti-human Vδ2 monoclonal antibody, and analyzed by flow cytometer. As a result, as shown in the panel on the left side in FIG. 4, Vδ2 positive γδ T cells accounted for 0.49% of lymphocyte gate. The peripheral blood mononuclear cells suspended in Yssel medium were reacted with ZOLF-POM (1 μM), cultured for 11 days together with IL-2, stained with PE-labeled anti-human CD3 monoclonal antibody and FITC-labeled anti-human Vδ2 monoclonal antibody, and analyzed by flow cytometer. As a result, as shown in the panel on the right side in FIG. 4, Vδ2 positive γδ T cells accounted for 98.29% of lymphocyte gate. This shows that Vδ2 positive γδ T cells with high purity can be easily prepared in a large amount in 11 days from the peripheral blood mononuclear cells of adult T cell leukemia patients by using ZOLF-POM.

Figure 5:
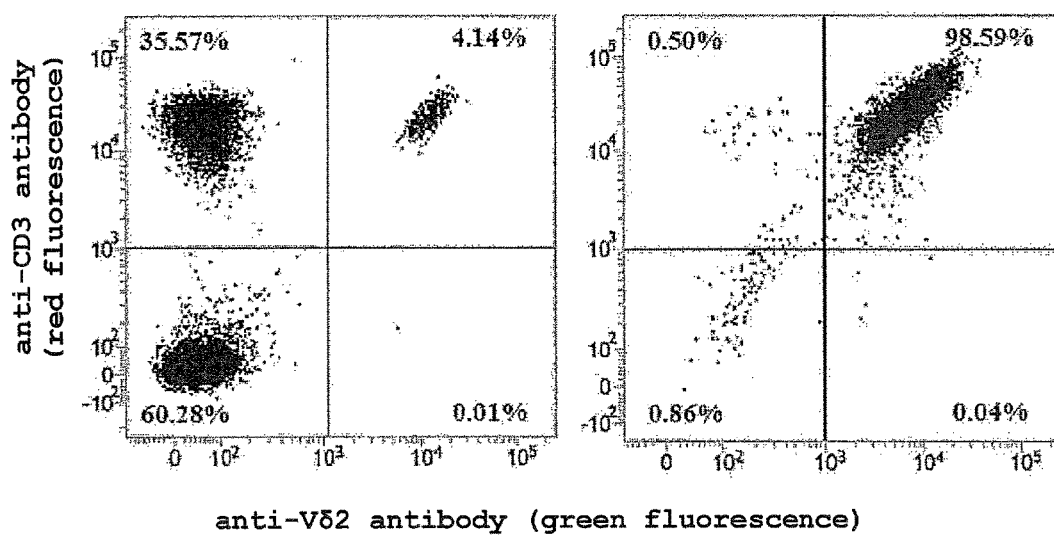
FIG. 5 shows the results of FACS analysis of peripheral blood mononuclear cells of lung cancer patient (1) which were stained with PE-labeled anti-human CD3 antibody and FITC-labeled anti-human Vδ2 antibody (left Figure). The results of FACS analysis of peripheral blood mononuclear cells of lung cancer patient (1) which were reacted with ZOLF-POM, cultured for 11 days together with IL-2, and stained with PE-labeled anti-human CD3 antibody and FITC labeled anti-human Vδ2 antibody (right Figure).

Experimental Example 4 (FIG. 5)

Heparin blood samples (peripheral blood 10 mL) were collected from lung cancer patients (1), and diluted with 10 ml of PBS. This was overlaid on 20 mL of Ficoll-Paque and subjected to density gradient centrifugation at 600×g for 30 min at room temperature. The layer directly above Ficoll-Paque was recovered, and washed 3 times with PBS to give peripheral blood mononuclear cells. The cells were suspended in 7 mL of Yssel medium, 1 mL therefrom was stained with PE-labeled anti-human CD3 monoclonal antibody and FITC-labeled anti-human Vδ2 monoclonal antibody, and analyzed by flow cytometer. As a result, as shown in the panel on the left side in FIG. 5, Vδ2 positive γδ T cells accounted for 4.14% of lymphocyte gate. The peripheral blood mononuclear cells suspended in Yssel medium were reacted with ZOLF-POM (1 μM), cultured for 11 days together with IL-2, stained with PE-labeled anti-human CD3 monoclonal antibody and FITC-labeled anti-human Vδ2 monoclonal antibody, and analyzed by flow cytometer. As a result, as shown in the panel on the right side in FIG. 5, Vδ2 positive γδ T cells accounted for 98.59% of lymphocyte gate. This shows that Vδ2 positive γδ T cells with high purity can be easily prepared in a large amount in 11 days from the peripheral blood mononuclear cells of lung cancer patients by using ZOLF-POM.

Figure 6:
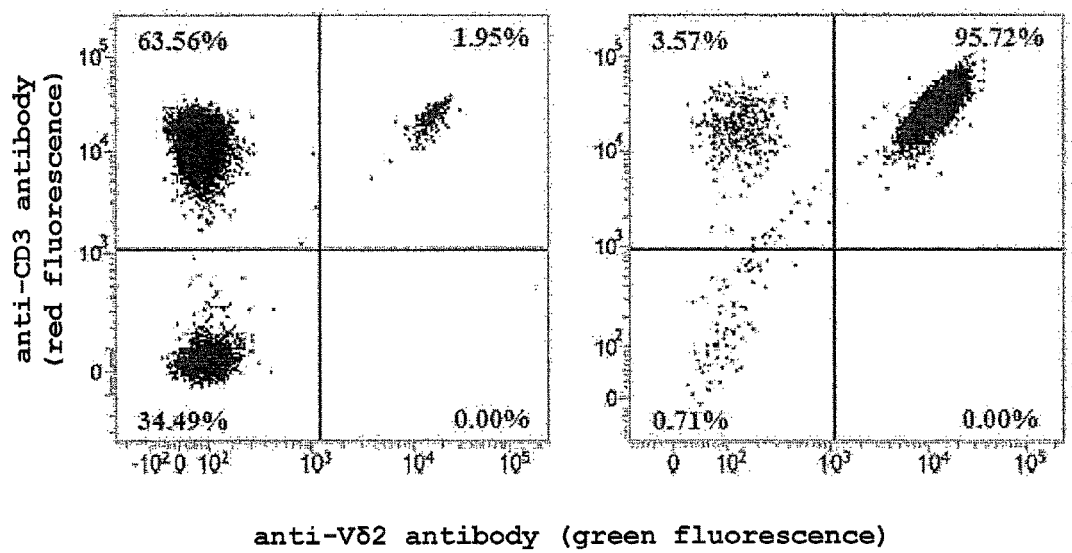
FIG. 6 shows the results of FACS analysis of peripheral blood mononuclear cells of lung cancer patient (2) which were stained with PE-labeled anti-human CD3 antibody and FITC-labeled anti-human Vδ2 antibody (left Figure). The results of FACS analysis of peripheral blood mononuclear cells of lung cancer patient (2) which were reacted with ZOLF-POM, cultured for 11 days together with IL-2, and stained with PE-labeled anti-human CD3 antibody and FITC labeled anti-human Vδ2 antibody (right Figure).

Experimental Example 5 (FIG. 6)

Heparin blood samples (peripheral blood 10 mL) were collected from lung cancer patients (2), and diluted with 10 mL of PBS. This was overlaid on 20 mL of Ficoll-Paque and subjected to density gradient centrifugation at 600×g for 30 min at room temperature. The layer directly above Ficoll-Paque was recovered, and washed 3 times with PBS to give peripheral blood mononuclear cells. The cells were suspended in 7 mL of Yssel medium, 1 mL therefrom was stained with PE-labeled anti-human CD3 monoclonal antibody and FITC-labeled anti-human Vδ2 monoclonal antibody, and analyzed by flow cytometer. As a result, as shown in the panel on the left side in FIG. 6, Vδ2 positive γδ T cells accounted for 1.95% of lymphocyte gate. The peripheral blood mononuclear cells suspended in Yssel medium were reacted with ZOLF-POM (1 μM), cultured for 11 days together with IL-2, stained with PE-labeled anti-human CD3 monoclonal antibody and FITC-labeled anti-human Vδ2 monoclonal antibody, and analyzed by flow cytometer. As a result, as shown in the panel on the right side in FIG. 6, Vδ2 positive γδ T cells accounted for 95.72% of lymphocyte gate. This shows that Vδ2 positive γδ T cells with high purity can be easily prepared in a large amount in 11 days from the peripheral blood mononuclear cells of lung cancer patients by using ZOLF-POM.

Methods using the fluorine-containing bisphosphonic acid or fluorine-containing bisphosphonate derivative of the present invention as an antitumor immunostimulating agent are specifically explained in Experimental Examples 6-19. An antitumor immunostimulation method using the compound of the present invention is not limited to those specifically explained in the following.

In the Experimental Examples, the following tumor cell lines were used as the target of the detection of tumor cytotoxicity assay of Vδ2 positive γδ T cells. The number after the name of the cell indicates the source of supply.

[Source of Supply]
(1) Health Science Research Resources Bank
(2) supplied by Dr. Tatsufumi Nakamura, Nagasaki University
(3) supplied by Dr. Yoichi Nakamura, Nagasaki University
monocyte tumor-derived U937 cells (U937)(1)
monocyte tumor-derived P31/FUJ cells (P31/FUJ)(1)
HCT-4 cells derived from HTLV-1 infected patients (HCT-4)(2)
HCT-5 cells derived from HTLV-1 infected patients (HCT-5)(2)
lung cancer-derived PC9 cells (PC9) (3)
urinary bladder cancer-derived EJ-1 cells (EJ-1)(1)

Figure 7:
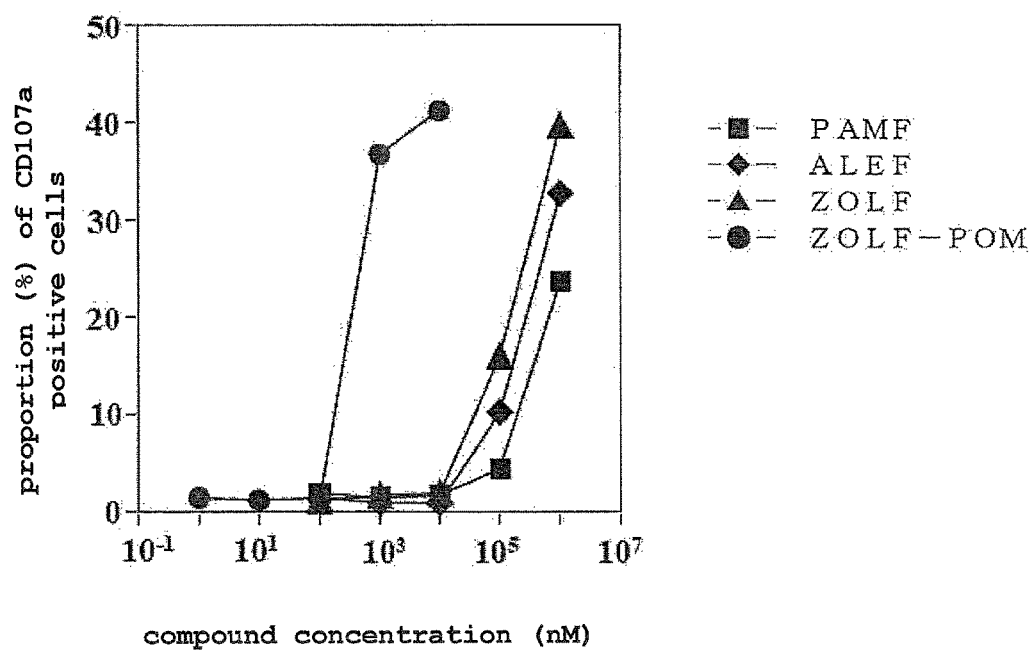
FIG. 7 shows when U937 (human histiocytic tumor cell) was reacted with PAMF, ALEF, ZOLF and ZOLF-POM at $10^0$-$10^6$ nM, Vδ2 positive γδ T cells derived from normal adult (1) were added, the cells were stained with PE-labeled anti-human CD107a antibody and FITC-labeled anti-human Vδ2 antibody and analyzed by FACS, and the proportion of CD107a positive cells in Vδ2 positive γδ T cells was determined. The proportion showed cytotoxicity and the compound concentration dependency thereof is summarized in the Figure.

Experimental Example 6 (FIG. 7)

Human histiocytic tumor cell line U937 cells were suspended in RPMI1640 medium at a cell concentration of 2×10$^5$/200 μL, and seeded by 200 μL in a 96 well round bottom plate. The plate was centrifuged at 600×g for 2 min, and the supernatant was removed. A dilution series of 100 nM, 1 μM, 10 μM, 100 μM, 1000 μM was prepared for PAMF, ALEF, ZOLF, and a dilution series of 1 nM, 10 nM, 100 nM, 1 μM, 10 μM was prepared for ZOLF-POM. The compound solutions of the dilution series were added by 200 μL to the cell pellets after removal of the supernatant and incubated at 37° C. for 2 hr. The cells were washed 3 times with RPMI1640 medium, and 50 μL of Vδ2 positive γδ T cells derived from normal adult (1) and having a cell concentration of 2×10$^5$/50 μL was added. Furthermore, PE-labeled anti-human CD107a monoclonal antibody (5 μL) was added, and the mixture was incubated at 37° C. for 2 hr. Thereto was added FITC-labeled anti-human Vδ2 monoclonal antibody (2 μL), and the mixture was incubated on ice for 20 min. This was washed 3 times with 2% FCS-added PBS, and suspended in 200 μL of 2% FCS-added PBS. This was analyzed by flow cytometer, the proportion of CD107a positive fractions in the Vδ2 positive cells was calculated, and the compound concentration dependency was summarized in the graph of FIG. 7. As a result, a compound concentration that induces maximum CD107a expression was several hundred μM for PAMF, ALEF, ZOLF, whereas about 100 nM for ZOLF-POM. From the foregoing, it was clarified that the sensitivity to a cytotoxicity activity of Vδ2 positive γδ T cells is promoted by reacting human histiocytic tumor cell line U937 with fluorine-containing bisphosphonic acid and a fluorine-containing bisphosphonate derivative.

Figure 8:
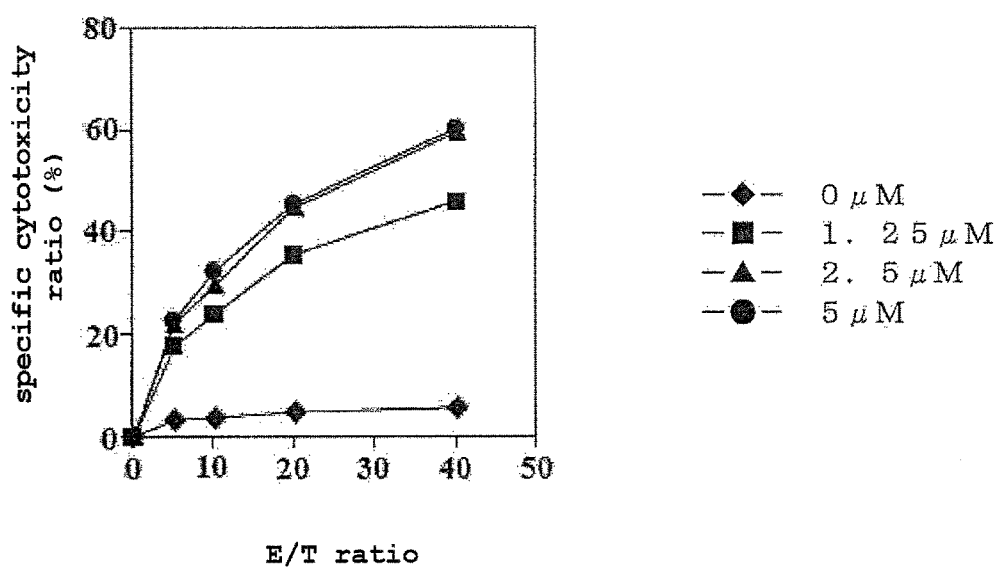
FIG. 8 shows when U937 (human histiocytic tumor cell) was reacted with ZOLF-POM at 0 μM, 1.25 μM, 2.5 μM or 5 μM, a chelating agent was added, the cells were washed, and Vδ2 positive γδ T cells derived from normal adult (1) were added. In this case, the proportion of U937 cells injured by Vδ2 positive γδ T cells was taken as a specific cytotoxicity ratio, and effector cell/target cell ratio (E/T ratio) dependency is summarized in the Figure.

Experimental Example 7 (FIG. 8)

Human histiocytic tumor cell line U937 cells were suspended in RPMI1640 medium at a cell concentration of 1×10$^6$/mL, and dispensed by 1 mL to a 15 mL conical tube. This was centrifuged at 600×g for 5 min, and the supernatant was removed. A dilution series of 0 μM, 1.25 μM, 2.5 μM, 5 μM was prepared for ZOLF-POM. The compound solutions of the dilution series were added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (1) were reacted at an effector cell/target cell ratio of 0:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 8. From the results, it was clarified that the sensitivity to a cytotoxicity activity of Vδ2 positive γδ T cells is promoted by reacting human histiocytic tumor cell line U937 with at least 1.25 μM ZOLF-POM.

Figure 9:
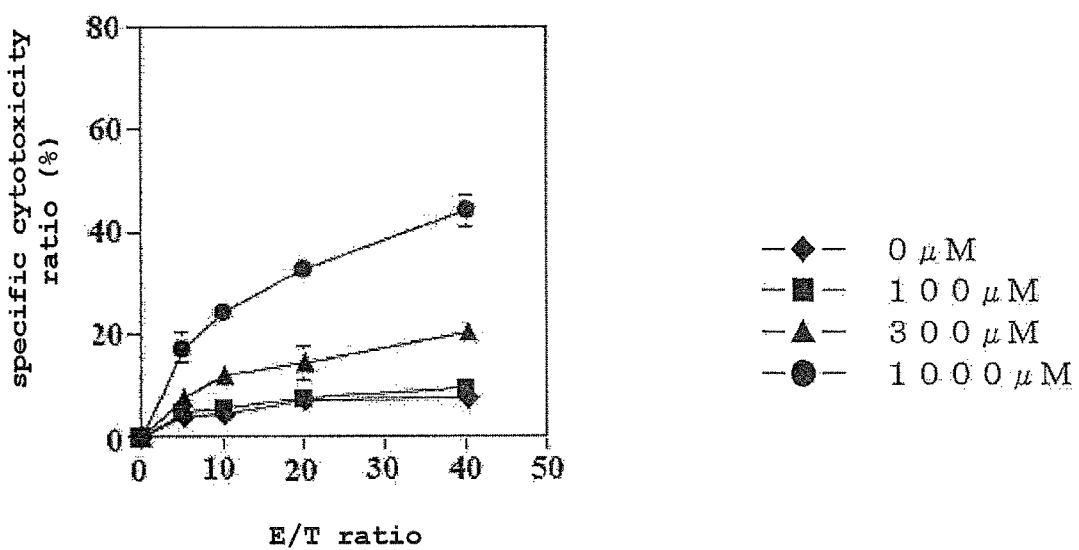
FIG. 9 shows when U937 (human histiocytic tumor cell) was reacted with ZOLF at 0 μM, 100 μM, 300 μM or 1000 μM, a chelating agent was added, the cells were washed, and Vδ2 positive γδ T cells derived from normal adult (1) were added. In this case, the proportion of U937 cells injured by Vδ2 positive γδ T cells was taken as a specific cytotoxicity ratio, and effector cell/target cell ratio (E/T ratio) dependency is summarized in the Figure.

Experimental Example 8 (FIG. 9)

Human histiocytic tumor cell line U937 cells were suspended in RPMI1640 medium at a cell concentration of 1×10$^6$/mL, and dispensed by 1 mL to a 15 mL conical tube. This was centrifuged at 600×g for 5 min, and the supernatant was removed. A dilution series of 0 μM, 100 μM, 300 μM, 1000 μM was prepared for ZOLF. The compound solutions of the dilution series were added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (1) were reacted at an effector cell/target cell ratio of 0:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 9. From the results, it was clarified that the sensitivity to a cytotoxicity activity of Vδ2 positive γδ T cells is promoted by reacting human histiocytic tumor cell line U937 with at least 300 μM ZOLF.

Figure 10:
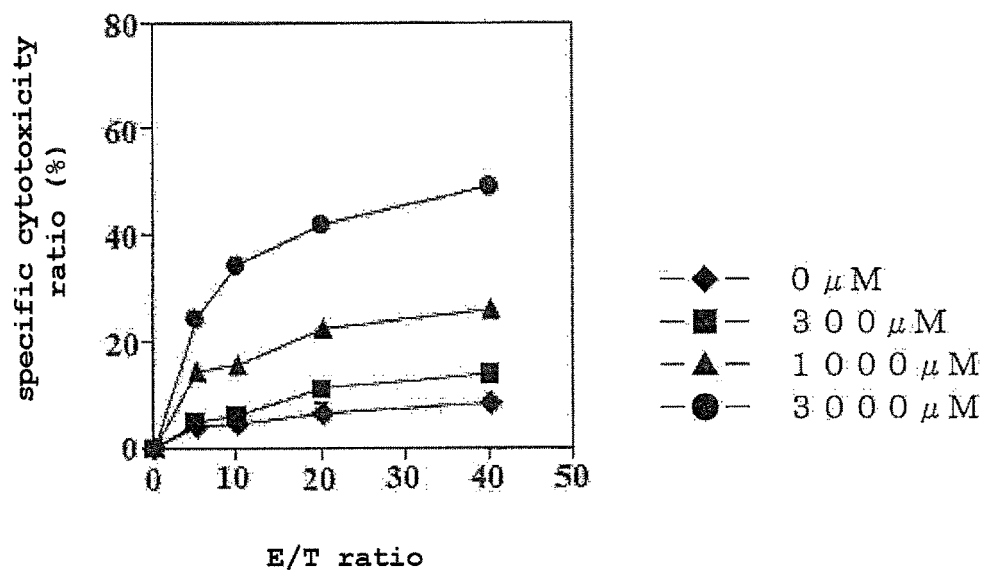
FIG. 10 shows when U937 (human histiocytic tumor cell) was reacted with ALEF at 0 μM, 300 μM, 1000 μM or 3000 μM, a chelating agent was added, the cells were washed, and Vδ2 positive γδ T cells derived from normal adult (1) were added. In this case, the proportion of U937 cells injured by Vδ2 positive γδ T cells was taken as a specific cytotoxicity ratio, and effector cell/target cell ratio (E/T ratio) dependency is summarized in the Figure.

Experimental Example 9 (FIG. 10)

Human histiocytic tumor cell line U937 cells were suspended in RPMI1640 medium at a cell concentration of 1×10$^6$/mL, and dispensed by 1 mL to a 15 mL conical tube. This was centrifuged at 600×g for 5 min, and the supernatant was removed. A dilution series of 0 μM, 300 μM, 1000 μM, 3000 μM was prepared for ALEF. The compound solutions of the dilution series were added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (1) were reacted at an effector cell/target cell ratio of 0:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 10. From the results, it was clarified that the sensitivity to a cytotoxicity activity of Vδ2 positive γδ T cells is promoted by reacting human histiocytic tumor cell line U937 with at least 300 μM ALEF.

Figure 11:
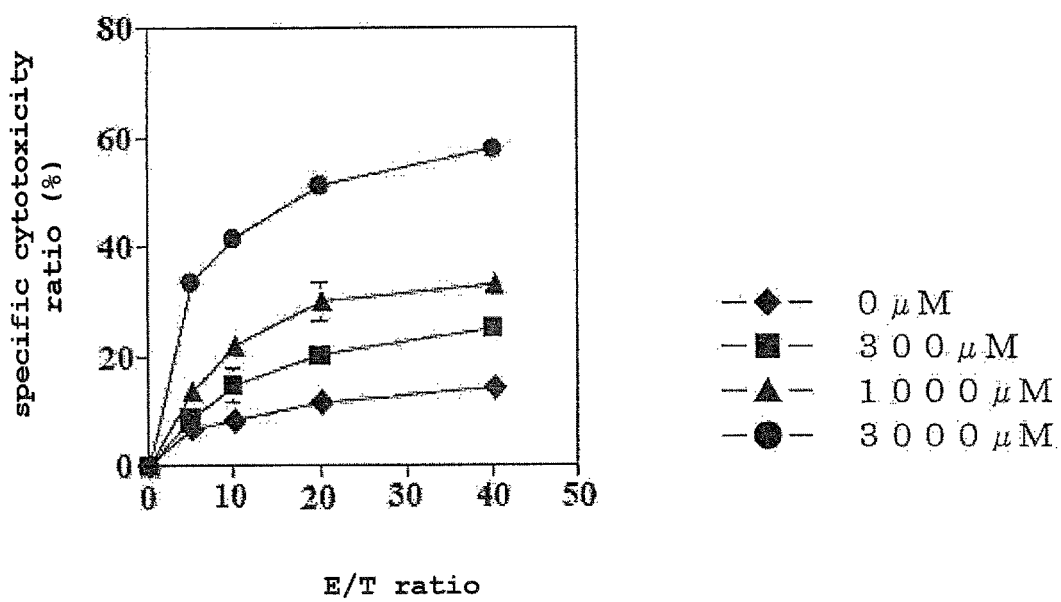
FIG. 11 shows when U937 (human histiocytic tumor cell) was reacted with PAMF at 0 μM, 300 μM, 1000 μM or 3000 μM, a chelating agent was added, the cells were washed, and Vδ2 positive γδ T cells derived from normal adult (1) were added. In this case, the proportion of U937 cells injured by Vδ2 positive γδ T cells was taken as a specific cytotoxicity ratio, and effector cell/target cell ratio (E/T ratio) dependency is summarized in the Figure.

Experimental Example 10 (FIG. 11)

Human histiocytic tumor cell line U937 cells were suspended in RPMI1640 medium at a cell concentration of 1×10$^6$/mL, and dispensed by 1 mL to a 15 mL conical tube. This was centrifuged at 600×g for 5 min, and the supernatant was removed. A dilution series of 0 μM, 300 μM, 1000 μM, 3000 μM was prepared for PAMF. The compound solutions of the dilution series were added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (1) were reacted at an effector cell/target cell ratio of 0:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 11. From the results, it was clarified that the sensitivity to a cytotoxicity activity of Vδ2 positive γδ T cells is promoted by reacting human histiocytic tumor cell line U937 with at least 300 μM PAMF.

Figure 12:
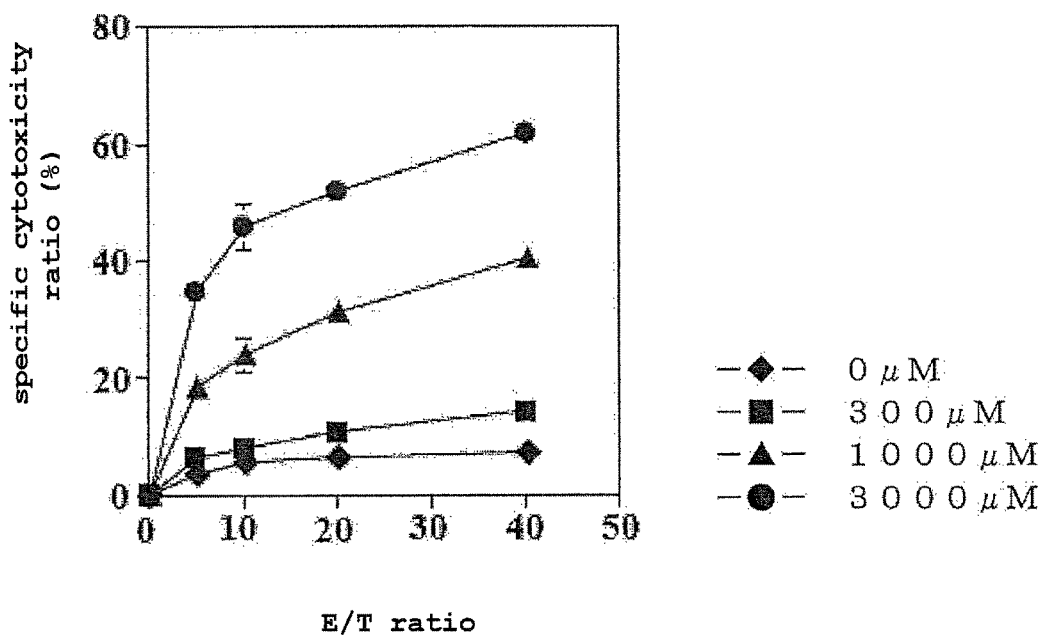
FIG. 12 shows when U937 (human histiocytic tumor cell) was reacted with IBAF at 0 μM, 300 μM, 1000 μM or 3000 μM, a chelating agent was added, the cells were washed, and Vδ2 positive γδ T cells derived from normal adult (1) were added. In this case, the proportion of U937 cells injured by Vδ2 positive γδ T cells was taken as a specific cytotoxicity ratio, and effector cell/target cell ratio (E/T ratio) dependency is summarized in the Figure.

Experimental Example 11 (FIG. 12)

Human histiocytic tumor cell line U937 cells were suspended in RPMI1640 medium at a cell concentration of 1×10$^6$/mL, and dispensed by 1 mL to a 15 mL conical tube. This was centrifuged at 600×g for 5 min, and the supernatant was removed. A dilution series of 0 μM, 300 μM, 1000 μM, 3000 μM was prepared for IBAF. The compound solutions of the dilution series were added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (1) were reacted at an effector cell/target cell ratio of 0:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 12. From the results, it was clarified that the sensitivity to a cytotoxicity activity of Vδ2 positive γδ T cells is promoted by reacting human histiocytic tumor cell line U937 with at least 300 μM IBAF.

Figure 13:
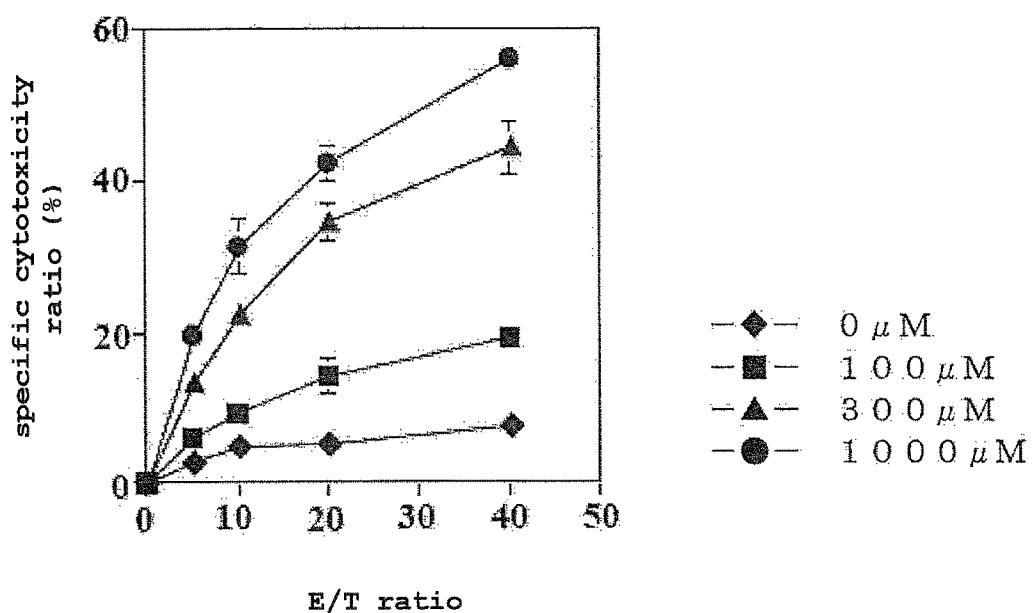
FIG. 13 shows when U937 (human histiocytic tumor cell) was reacted with ZOLF at 0 μM, 100 μM, 300 μM or 1000 μM, a chelating agent was added, the cells were washed, and Vδ2 positive γδ T cells derived from normal adult (2) were added. In this case, the proportion of U937 cells injured by Vδ2 positive γδ T cells was taken as a specific cytotoxicity ratio, and effector cell/target cell ratio (E/T ratio) dependency is summarized in the Figure.

Experimental Example 12 (FIG. 13)

Human histiocytic tumor cell line U937 cells were suspended in RPMI1640 medium at a cell concentration of 1×10$^6$/mL, and dispensed by 1 mL to a 15 mL conical tube. This was centrifuged at 600×g for 5 min, and the supernatant was removed. A dilution series of 0 μM, 100 μM, 300 μM, 1000 μM was prepared for ZOLF. The compound solutions of the dilution series were added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (2) were reacted at an effector cell/target cell ratio of 0:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 13. From the results, it was clarified that the sensitivity to a cytotoxicity activity of Vδ2 positive γδ T cells is promoted by reacting human histiocytic tumor cell line U937 with at least 300 μM ZOLF.

Figure 14:
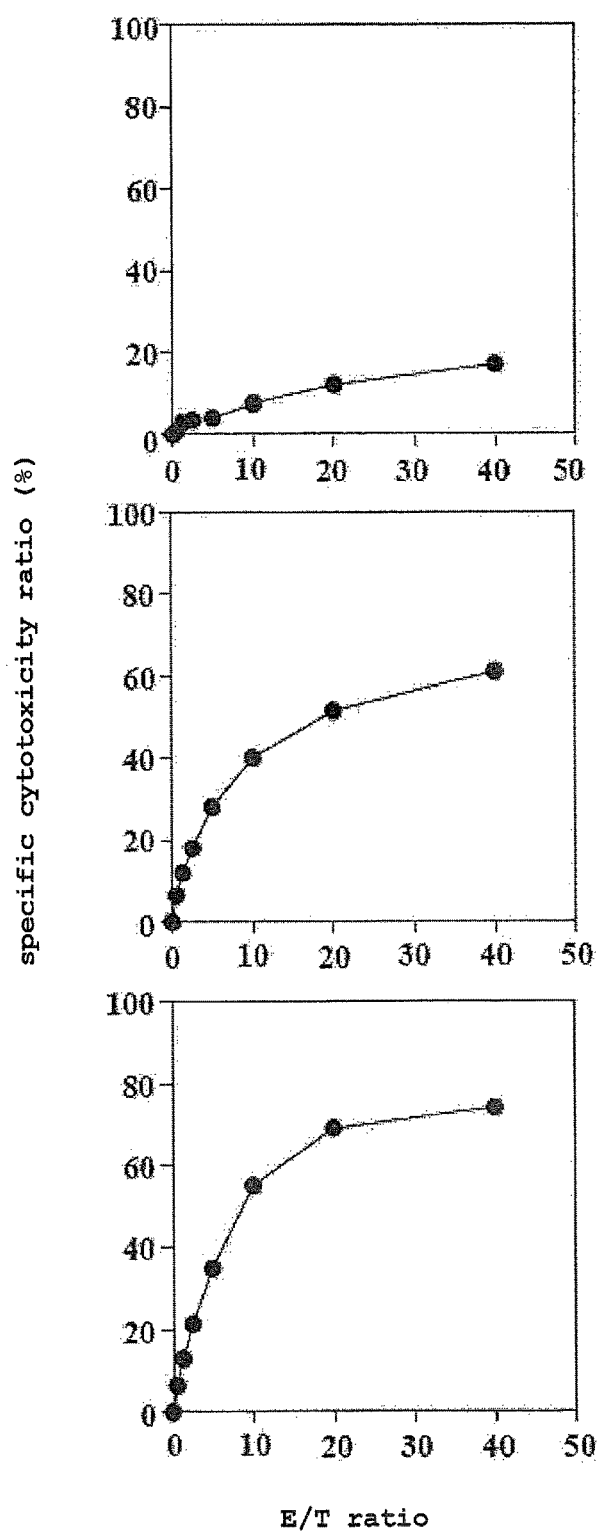
FIG. 14 shows when U937 (human histiocytic tumor cell) was reacted with a medium (upper panel), ZOLF 500 μM (middle panel), or ZOLF-POM 5 μM (lower panel), a chelating agent was added, the cells were washed, and Vδ2 positive γδ T cells derived from normal adult (3) were added. In this case, the proportion of U937 cells injured by Vδ2 positive γδ T cells was taken as a specific cytotoxicity ratio, and effector cell/target cell ratio (E/T ratio) dependency is summarized in the Figure.

Experimental Example 13 (FIG. 14)

Human histiocytic tumor cell line U937 cells were suspended in RPMI1640 medium at a cell concentration of 1×10$^6$/mL, and dispensed by 1 mL to a 15 mL conical tube. This was centrifuged at 600×g for 5 min, and the supernatant was removed. The medium, ZOLF 500 μM solution or ZOLF-POM 5 μM solution was added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (3) were reacted at an effector cell/target cell ratio of 0.625:1, 1.25:1, 2.5:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 14. From the results, it was clarified that the sensitivity to a cytotoxicity activity of Vδ2 positive γδ T cells is promoted by reacting human histiocytic tumor cell line U937 with at least 500 μM ZOLF or 5 μM ZOLF-POM.

Figure 15:
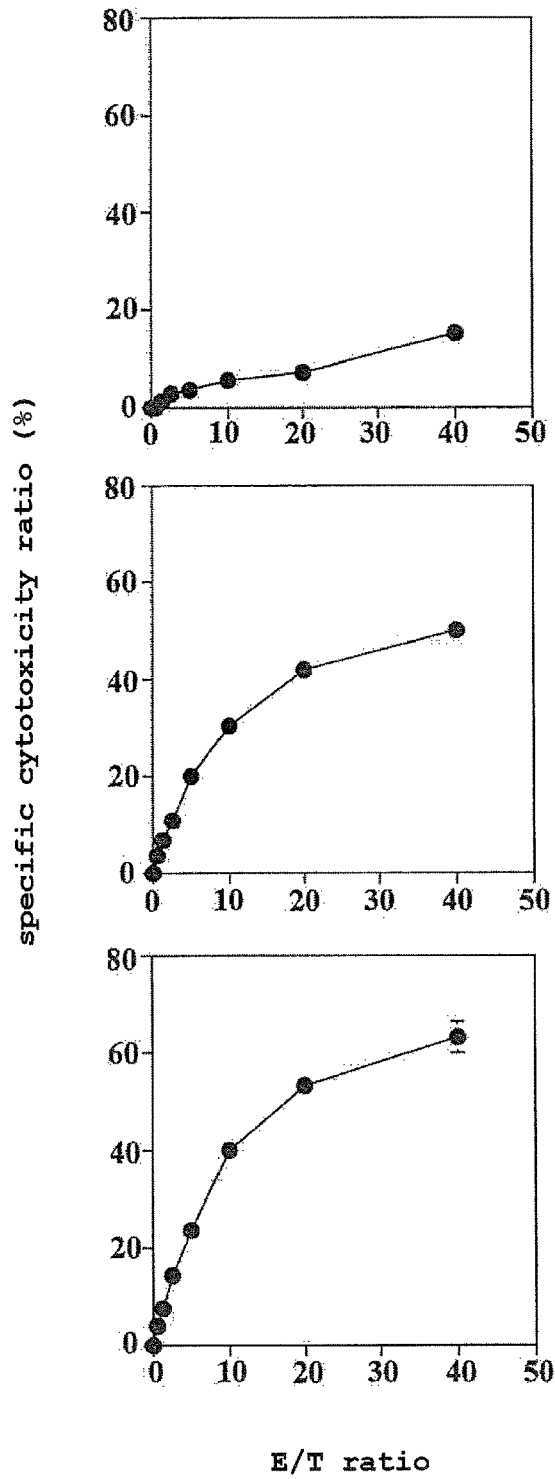
FIG. 15 shows when U937 (human histiocytic tumor cell) was reacted with a medium (upper panel), ZOLF 500 μM (middle panel), or ZOLF-POM 5 μM (lower panel), a chelating agent was added, the cells were washed, and Vδ2 positive γδ T cells derived from normal adult (4) were added. In this case, the proportion of U937 cells injured by Vδ2 positive γδ T cells was taken as a specific cytotoxicity ratio, and effector cell/target cell ratio (E/T ratio) dependency is summarized in the Figure.

Experimental Example 14 (FIG. 15)

Human histiocytic tumor cell line U937 cells were suspended in RPMI1640 medium at a cell concentration of $1 \times 10^6$/mL, and dispensed by 1 mL to a 15 mL conical tube. This was centrifuged at 600×g for 5 min, and the supernatant was removed. The medium, ZOLF 500 μM solution or ZOLF-POM 5 μM solution was added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (4) were reacted at an effector cell/target cell ratio of 0.625:1, 1.25:1, 2.5:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 15. From the results, it was clarified that the sensitivity to a cytotoxicity activity of Vδ2 positive γδ T cells is promoted by reacting human histiocytic tumor cell line U937 with at least 500 μM ZOLF or 5 μM ZOLF-POM.

Figure 16:
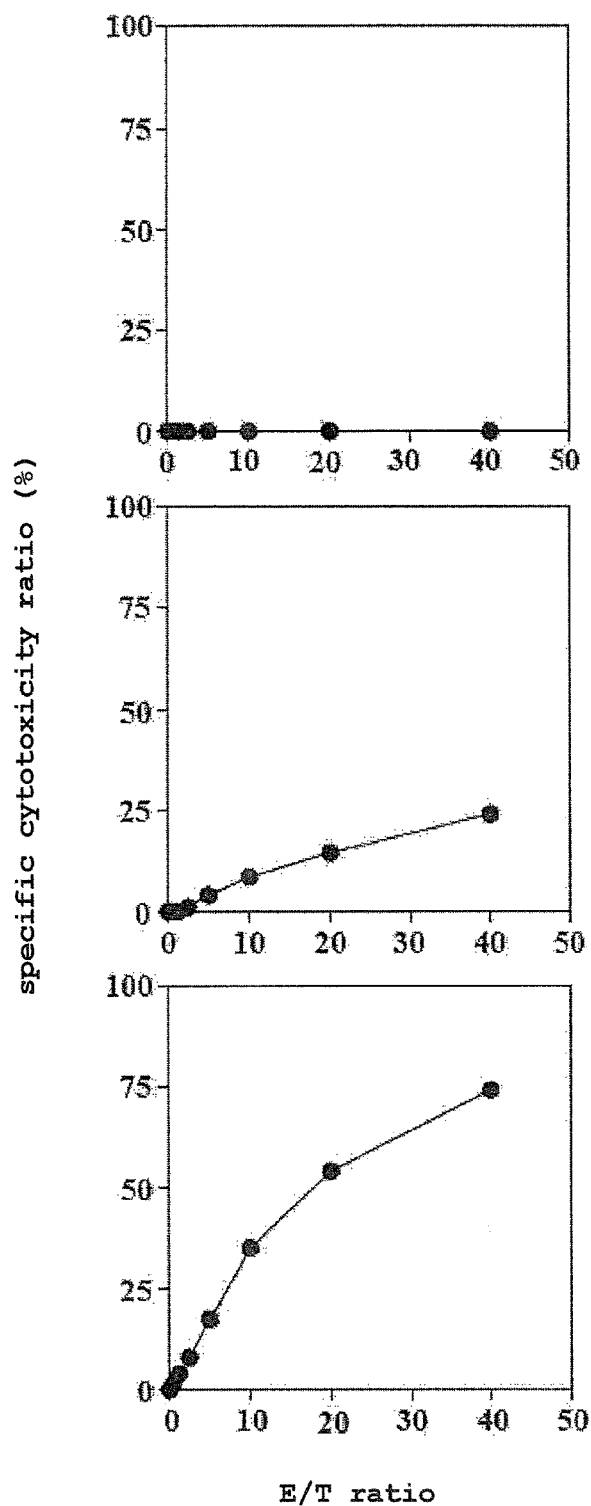
FIG. 16 shows when human monocytic tumor cells P31/FUJ were reacted with a medium (upper panel), ZOLF 500 μM (middle panel), or ZOLF-POM 5 μM (lower panel), a chelating agent was added, the cells were washed, and Vδ2 positive γδ T cells derived from normal adult (3) were added. In this case, the proportion of P31/FUJ cells injured by Vδ2 positive γδ T cells was taken as a specific cytotoxicity ratio, and effector cell/target cell ratio (E/T ratio) dependency is summarized in the Figure.

Experimental Example 15 (FIG. 16)

Human monocyte tumor cell line P31/FUJ cells were suspended in RPMI1640 medium at a cell concentration of $1 \times 10^6$/mL, and dispensed by 1 mL to a 15 mL conical tube. This was centrifuged at 600×g for 5 min, and the supernatant was removed. The medium, ZOLF 500 μM solution or ZOLF-POM 5 μM solution was added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (3) were reacted at an effector cell/target cell ratio of 0.625:1, 1.25:1, 2.5:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 16. From the results, it was clarified that the sensitivity to a cytotoxicity activity of Vδ2 positive γδ T cells is promoted by reacting human monocyte tumor cell line P31/FUJ with at least 500 μM ZOLF or 5 μM ZOLF-POM.

Figure 17:
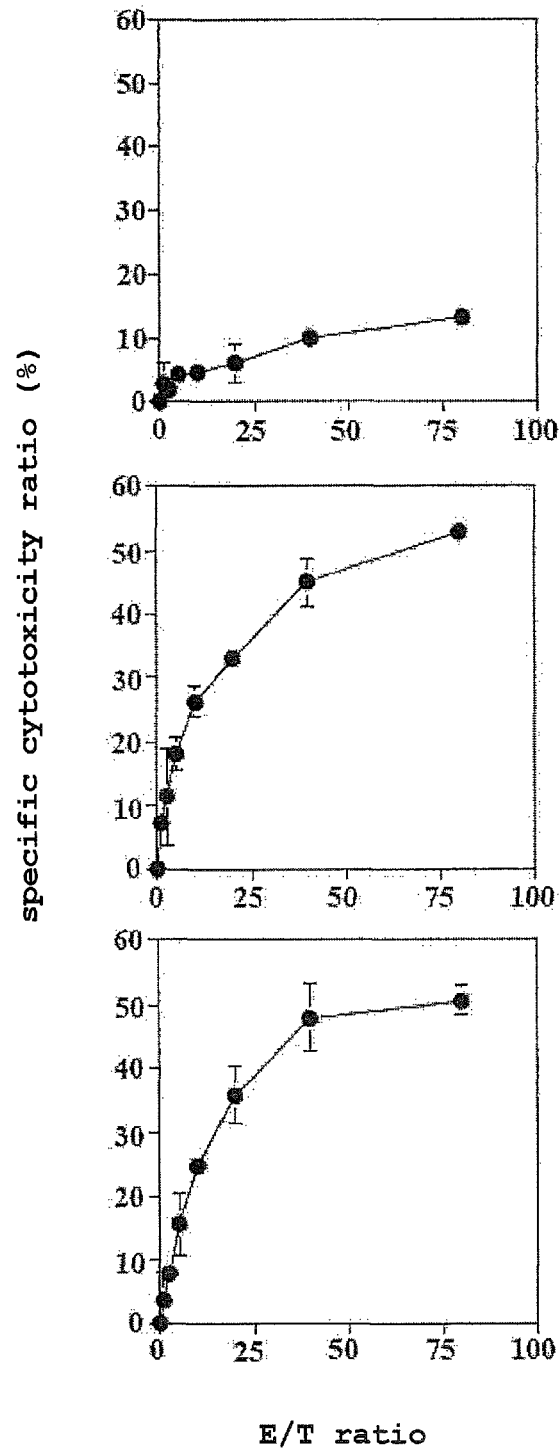
FIG. 17 shows when adult T cell leukemia cell line HCT-5 was reacted with a medium (upper panel), ZOLF 1 mM (middle panel), or ZOLF-POM 1 μM (lower panel), a chelating agent was added, the cells were washed, and Vδ2 positive γδ T cells derived from normal adult (4) were added. In this case, the proportion of HCT-5 cells injured by Vδ2 positive γδ T cells was taken as a specific cytotoxicity ratio, and effector cell/target cell ratio (E/T ratio) dependency is summarized in the Figure.

Experimental Example 16 (FIG. 17)

Adult T cell leukemia cell line HCT-5 cells were suspended in RPMI1640 medium at a cell concentration of $1 \times 10^6$/mL, and dispensed by 1 mL to a 15 mL conical tube. This was centrifuged at 600×g for 5 min, and the supernatant was removed. The medium, ZOLF 1 mM solution or ZOLF-POM 1 μM solution was added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from adult T cell leukemia patients (4) were reacted at an effector cell/target cell ratio of 1.25:1, 2.5:1, 5:1, 10:1, 20:1, 40:1, 80:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 17. From the results, it was clarified that the sensitivity to a cytotoxicity activity of Vδ2 positive γδ T cells is promoted by reacting adult T cell leukemia cell line HCT-5 with at least 1 mM ZOLF or 1 μM ZOLF-POM.

Figure 18:
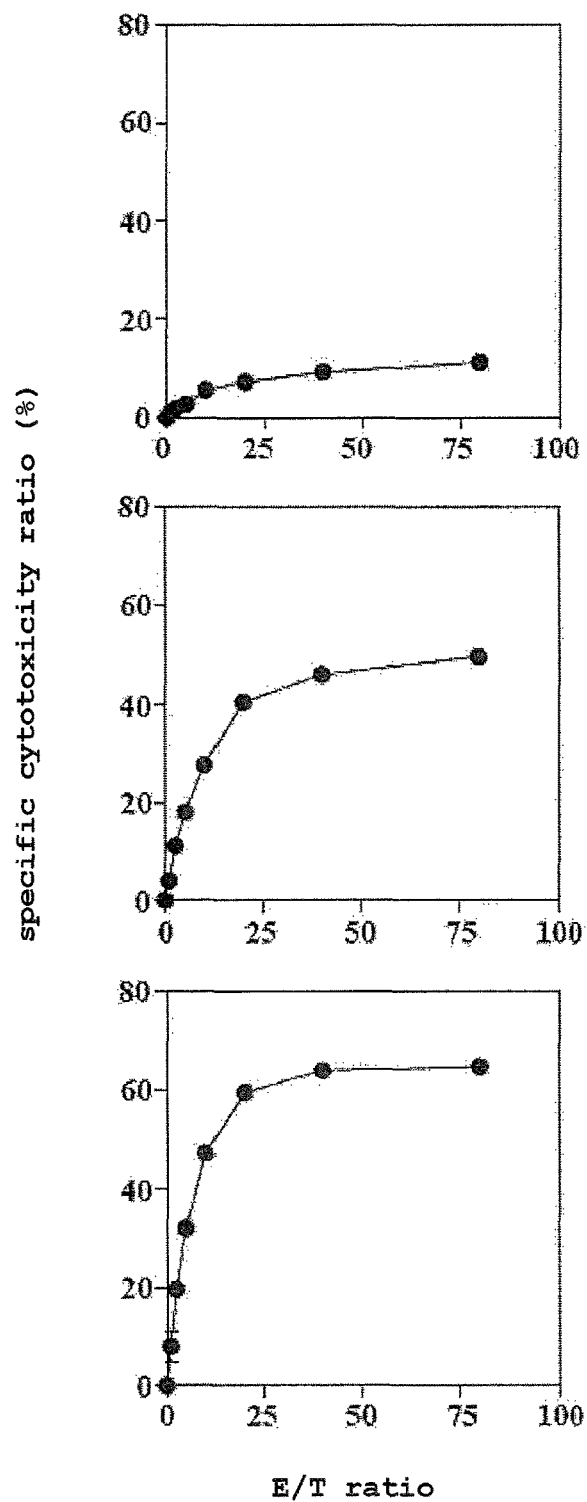
FIG. 18 shows when adult T cell leukemia cell line HCT-4 was reacted with a medium (upper panel), ZOLF-POM 1 μM (middle panel), or ZOLF-POM 10 μM, a chelating agent was added, the cells were washed, and Vδ2 positive γδ T cells derived from normal adult (4) were added. In this case, the proportion of HCT-4 cells injured by Vδ2 positive γδ T cells was taken as a specific cytotoxicity ratio, and effector cell/target cell ratio (E/T ratio) dependency is summarized in the Figure.

Experimental Example 17 (FIG. 18)

Adult T cell leukemia cell line HCT-4 cells were suspended in RPMI1640 medium at a cell concentration of $1 \times 10^6$/mL, and dispensed by 1 mL to a 15 mL conical tube. This was centrifuged at 600×g for 5 min, and the supernatant was removed. The medium, ZOLF-POM 1 μM solution or ZOLF-POM 10 μM solution was added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from adult T cell leukemia patients (4) were reacted at an effector cell/target cell ratio of 1.25:1, 2.5:1, 5:1, 10:1, 20:1, 40:1, 80:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 18. From the results, it was clarified that the sensitivity to a cytotoxicity activity of Vδ2 positive γδ T cells is promoted by reacting adult T cell leukemia cell line HCT-4 with at least 1 μM ZOLF-POM.

Figure 19:
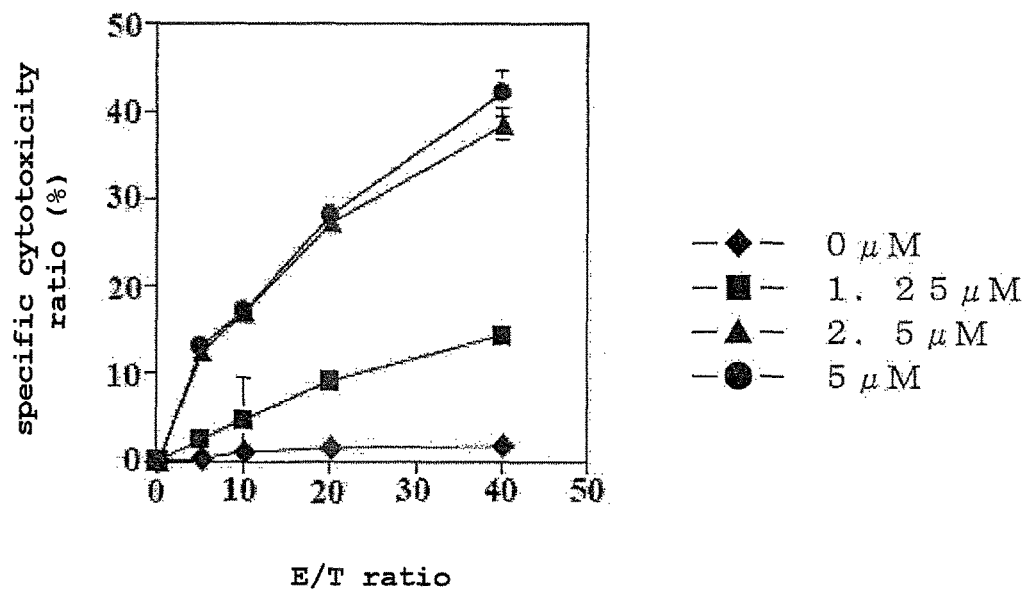
FIG. 19 shows when human lung cancer cell line PC9 was reacted with ZOLF-POM at 0 μM, 1.25 μM, 2.5 μM or 5 μM, a chelating agent was added, the cells were washed, and Vδ2 positive γδ T cells derived from lung cancer patient (1) were added. In this case, the proportion of PC9 cells injured by Vδ2 positive γδ T cells was taken as a specific cytotoxicity ratio, and effector cell/target cell ratio (E/T ratio) dependency is summarized in the Figure.

Experimental Example 18 (FIG. 19)

Human lung cancer cell line PC9 cells were suspended in RPMI1640 medium at a cell concentration of $1\times10^6$/mL, and dispensed by 1 mL to a 15 mL conical tube. This was centrifuged at 600×g for 5 min, and the supernatant was removed. A dilution series of 0 μM, 1.25 μM, 2.5 μM, 5 μM was prepared for ZOLF-POM. The compound solutions of the dilution series were added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from lung cancer patients (1) were reacted at an effector cell/target cell ratio of 0:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 19. From the results, it was clarified that the sensitivity to a cytotoxicity activity of Vδ2 positive γδ T cells is promoted by reacting human lung cancer cell line PC9 with at least 1.25 μM ZOLF-POM.

Figure 20:
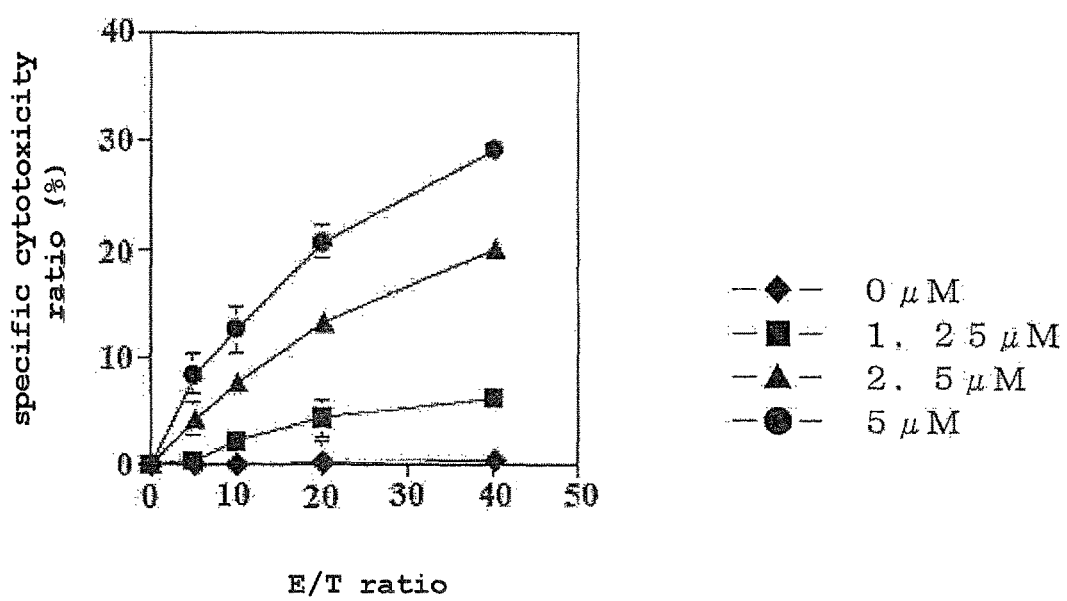
FIG. 20 shows when human bladder cancer cell line EJ-1 was reacted with ZOLF-POM at 0 μM, 1.25 μM, 2.5 μM or 5 μM, a chelating agent was added, the cells were washed, and Vδ2 positive γδ T cells derived from normal adult (1) were added. In this case, the proportion of EJ-1 cells injured by Vδ2 positive γδ T cells was taken as a specific cytotoxicity ratio, and effector cell/target cell ratio (E/T ratio) dependency is summarized in the Figure.

Experimental Example 19 (FIG. 20)

Human bladder cancer cell line EJ-1 cells were suspended in RPMI1640 medium at a cell concentration of $1\times10^6$/mL, and dispensed by 1 mL to a 15 mL conical tube. This was centrifuged at 600×g for 5 min, and the supernatant was removed. A dilution series of 0 μM, 1.25 μM, 2.5 μM, 5 μM was prepared for ZOLF-POM. The compound solutions of the dilution series were added by 1 mL to the cell pellets after removal of the supernatant and incubated at 37° C. for 1 hr 45 min. Thereto was added 10 mM lanthanoid metal chelating agent by 2.5 μL, and the mixture was further incubated for 15 min. These conical tubes were centrifuged at 600×g for 5 min, and the cell pellets were washed 3 times with RPMI1640 medium. Then, the cell pellets were suspended in 5 mL of RPMI1640 medium, 2 mL therefrom was placed in a different conical tube, and 6 mL of RPMI1640 medium was further added. The cell suspension was seeded by 100 μL in a 96 well round bottom plate. Vδ2 positive γδ T cells derived from normal adult (1) were reacted at an effector cell/target cell ratio of 0:1, 5:1, 10:1, 20:1, 40:1, and incubated for 40 min at 37° C. The plate was centrifuged at 600×g for 2 min, 25 μL of culture supernatant was taken, and diluted with 200 μL of europium-added acetate buffer. The mixture was taken by 200 μL, and time-resolved fluorescence was measured. The specific cytotoxicity rate was determined from the value of each sample, and the effector cell/target cell ratio dependency was graphically shown in FIG. 20. From the results, it was m clarified that the sensitivity to a cytotoxicity activity of Vδ2 positive γδ T cells is promoted by reacting human bladder cancer cell line EJ-1 with at least 1.25 μM ZOLF-POM.

INDUSTRIAL APPLICABILITY

The novel fluorine-containing bisphosphonic acid or fluorine-containing bisphosphonate derivative of the present invention becomes a superior Vδ2 positive γδ T cell activator when it is reacted with the peripheral blood. When it is reacted with tumor cells or virus infected cells, it promotes sensitivity to a cytotoxicity action of Vδ2 positive γδ T cells, and functions as an antitumor or antiviral agent. From these findings, antitumor immunotherapy and antiviral infection treating method using the novel fluorine-containing bisphosphonic acid and/or a fluorine-containing bisphosphonate derivative of the present invention can be established. Specifically, peripheral blood mononuclear cells of cancer patients or virus infection patients are prepared, and cultured ex vivo in the presence of the novel fluorine-containing bisphosphonic acid or fluorine-containing bisphosphonate derivative of the present invention and IL-2 to induce proliferation of Vδ2 positive γδ T cells. The cells are intravenously or topically administered to the patients, whereby immunotherapy of cancer and virus infection, which utilizes Vδ2 positive γδ T cells, becomes possible. In addition, immunotherapy of cancer and virus infection, which utilizes Vδ2 positive γδ T cells, becomes possible by directly administering the novel fluorine-containing bisphosphonic acid or fluorine-containing bisphosphonate derivative of the present invention to cancer patients or virus infection patients. In this case, the novel fluorine-containing bisphosphonic acid or fluorine-containing bisphosphonate derivative of the present invention is incorporated into monocyte cells, and the fluorine-containing bisphosphonic acid directly inhibits farnesyl diphosphate synthase, and the fluorine-containing bisphosphonate derivative undergoes hydrolysis of the ester, is converted to fluorine-containing bisphosphonic acid and inhibits farnesyl diphosphate synthase. Due to the inhibitory action, isopentenyl diphosphate, which is a metabolite located directly upstream of the enzyme, is intracellularly accumulated. Isopentenyl diphosphate binds to an intracellular region of the butyrophilin 3A1 molecule present in the cellular membrane, and changes the conformation of the extracellular region or changes the degree of polymerization. The change is recognized by Vδ2 positive γδ T cells, and proliferation stimulation is produced. The proliferated γδ T cells show high tumor cytotoxicity, and high virus infected cell toxicity. On the other hand, the novel fluorine-containing bisphosphonic acid or fluorine-containing bisphosphonate derivative of the present invention is incorporated into tumor cells and virus infected cells, during which a phenomenon similar to the changes in the monocytes occurs. That is, the fluorine-containing bisphosphonic acid directly inhibits farnesyl diphosphate synthase, and the fluorine-containing bisphosphonate derivative undergoes hydrolysis of the ester, is converted to the form of an acid and inhibits farnesyl diphosphate synthase. Due to the inhibitory action, isopentenyl diphosphate, which is a metabolite located directly upstream of the enzyme, is intracellularly accumulated. Isopentenyl diphosphate binds to an intracellular region of the butyrophilin 3A1 molecule present in the cellular membrane, and changes the conformation of the extracellular region or changes the degree of polymerization. The change is recognized by Vδ2 positive

The invention claimed is:

1. A compound represented by formula (I):

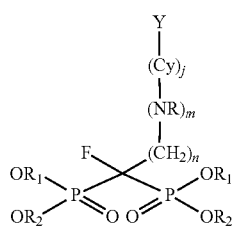

wherein Cy is an imidazolyl group, Y is a hydrogen atom, F is a fluorine atom, P is a phosphorus atom, $R_1$ and $R_2$ are the same or different from each other and each is an alkylcarbonyloxyalkyl group, j is a number 1, m is a number 0, and n is an integer of 1-6,
or a pharmaceutically acceptable salt thereof.

2. The compound according to claim 1, wherein $R_1$ and $R_2$ are the same or different and each is a $C_{2-7}$ alkylcarbonyloxy-$C_{1-3}$ alkyl group, or a pharmaceutically acceptable salt thereof.

3. The compound according to claim 1, wherein $R_1$ and $R_2$ are the same or different and each is pivaloyloxymethyl (POM) group, or a pharmaceutically acceptable salt thereof.

4. The compound according to claim 1, which is a compound represented by formula (5)

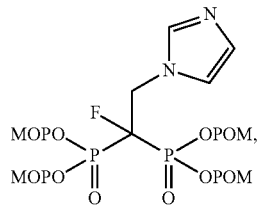

or a pharmaceutically acceptable salt thereof.

5. A pharmaceutical composition comprising the compound according to claim 1, or a pharmaceutically acceptable salt thereof, as an active ingredient.

6. A pharmaceutical composition comprising the compound according to claim 2, or a pharmaceutically acceptable salt thereof, as an active ingredient.

7. A pharmaceutical composition comprising the compound according to claim 3, or a pharmaceutically acceptable salt thereof, as an active ingredient.

8. A pharmaceutical composition comprising the compound according to claim 4, or a pharmaceutically acceptable salt thereof, as an active ingredient.

9. A method of (i) treating a lymphocyte in a living body, (ii) proliferating and/or inducing a γδ T cell, (iii) suppressing proliferation of a tumor cell, or (iv) treating cancer, comprising administering an effective amount of the compound according to claim 1, or a pharmaceutically acceptable salt thereof, to a living body.

10. A method of proliferating and/or inducing a γδ T cell, comprising reacting ex vivo the compound according to claim 1, or a pharmaceutically acceptable salt thereof, with a sample containing γδ T cells.

11. A method of suppressing proliferation of a tumor cell, comprising a step of reacting the compound according to claim 1, or a pharmaceutically acceptable salt thereof, with a sample containing γδ T cells collected from a living body, and a step of returning the γδ T cells to the living body.

* * * * *